US008147798B2

(12) United States Patent
Klunk et al.

(10) Patent No.: US 8,147,798 B2
(45) Date of Patent: Apr. 3, 2012

(54) AMYLOID IMAGING AS A SURROGATE MARKER FOR EFFICACY OF ANTI-AMYLOID THERAPIES

(75) Inventors: William E. Klunk, Pittsburgh, PA (US); Chester A. Mathis, Jr., Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 1156 days.

(21) Appl. No.: 11/666,083

(22) PCT Filed: Jul. 1, 2005

(86) PCT No.: PCT/US2005/023617
§ 371 (c)(1),
(2), (4) Date: Nov. 28, 2007

(87) PCT Pub. No.: WO2006/014381
PCT Pub. Date: Feb. 9, 2006

(65) Prior Publication Data
US 2008/0219931 A1    Sep. 11, 2008

Related U.S. Application Data

(60) Provisional application No. 60/584,487, filed on Jul. 2, 2004.

(51) Int. Cl.
*A61K 49/00* (2006.01)
*A61K 51/00* (2006.01)
(52) U.S. Cl. ...... 424/1.1; 424/1.65; 424/1.81; 424/1.89; 424/9.1; 424/9.8

(58) Field of Classification Search ................. 424/1.11, 424/1.65, 1.89, 9.1–9.8; 435/6, 199
See application file for complete search history.

(56) References Cited

U.S. PATENT DOCUMENTS

| 7,270,800 B2* | 9/2007 | Klunk et al. ................. 424/1.89 |
| 2003/0092003 A1* | 5/2003 | Blatt et al. ........................ 435/6 |

(Continued)

FOREIGN PATENT DOCUMENTS
WO    WO 02/16333  A2    2/2002
(Continued)

OTHER PUBLICATIONS

Zhi-Ping Zhuang et al., "IBOX (2-(4'-dimethylaminophenyl)-6-iodobenzoxazole): a ligand for imaging amyloid plaques in the brain", Nuclear Medicine and Biology 28 (2001) 887-894.

(Continued)

*Primary Examiner* — Michael G Hartley
*Assistant Examiner* — Jagadishwar Samala
(74) *Attorney, Agent, or Firm* — Stephen A. Bent; Foley & Lardner LLP

(57) ABSTRACT

The present method for determining the efficacy of therapy in the treatment of amyloidosis involves administering to a patient in need thereof a compound of formula (I) or Formula (II) or structures 1-45 and imaging the patient. After said imaging, at least one anti-amyloid agent is administered to said patient. Then, an effective amount of a compound of formula (I) or Formula (II) or structures 1-45 is administered to the patient and the patient is imaged again. Finally, baseline levels of amyloid deposition in the patient before treatment with the anti-amyloid agent are compared with levels of amyloid deposition in the patient following treatment with the anti-amyloid agent.

1 Claim, 5 Drawing Sheets

U.S. PATENT DOCUMENTS

2003/0236391 A1* 12/2003 Klunk et al. .................... 534/11

FOREIGN PATENT DOCUMENTS

| WO | WO 02/085903 A2 | 10/2002 |
|----|-----------------|---------|
| WO | WO 03/051859 A1 | 6/2003 |
| WO | WO 03/068269 A1 | 8/2003 |
| WO | WO 2004/083195 A1 | 9/2004 |
| WO | WO 2004/087684 A1 | 10/2004 |
| WO | WO 2006/014382 A1 | 2/2006 |

OTHER PUBLICATIONS

W. Klunk et al., "Imaging Brain Amyloid in Alzheimer's Disease with Pittsburgh Compound-B", Ann Neurol 2004;55:306-319.

A. Nordberg, "Toward an Early Diagnosis and Treatment of Alzheimer's Disease", International Psychogeriatrics, vol. 15, No. 3, 2003, pp. 223-237.

Y. Wang et al., "Synthesis and Evaluation of a Radioiodinated Benzothiazole Derivative as a Radioligand for In Vivo Quantitation of β-Amyloid Deposits in Aging and Alzheimer's Disease", J. Labelled Cpd. Radiopharm, 44, Suppl. 1 (2001), S239-S241.

Y. Wang et al., "Synthesis and Evaluation of 2-(3'-Iodo-4'-aminophenyl)-6-hydroxybenzothiazole for In Vivo Quantitation of Amyloid Deposits in Alzheimer's Disease", Journal of Molecular Neuroscience, vol. 19 (2002) pp. 11-16.

K.A. Johnson MD et al., "Preclinical prediction of Alzheimer's disease using SPECT", Neurology 50, Jun. 1998, pp. 1563-1571.

C. M. Clark et al., "Alzheimer Disease: Current Concepts and Emerging Diagnostic and Therapeutic Strategies", Annals of Internal Medicine, vol. 138, No. 5, Mar. 4, 2003, pp. 400-410.

C. Hock et al., "Antibodies against β-Amyloid Slow Cognitive Decline in Alzheimer's Disease", Neuron, vol. 38, 547-554, May 22, 2003.

Japanese Office Action Patent Application No. 2007-519500 mailed May 10, 2011.

Brian J. Bacskai et al., "Imaging of amyloid-β deposits in brains of living mice permits direct observation of clearance of plaques with immunotherapy", Nature Medicine, vol. 7, No. 3, Mar. 2001, pp. 369-372.

* cited by examiner

AMYLOID IMAGING AS A SURROGATE MARKER FOR EFFICACY OF ANTI-AMYLOID THERAPIES

BACKGROUND

Amyloidosis is a diverse group of disease processes characterized by extracellular tissue deposits, in one or many organs, of protein materials which are generically termed amyloid. Amyloid may be distinguished grossly by a starch-like staining reaction with iodine (thus the term amyloid), microscopically by its extracellular distribution and tinctorial and optical properties when stained with Congo red, and by its protein fibril structure as shown by electron microscopy and x-ray crystallography (see Table 1). Exemplary amyloidosis diseases are Alzheimer's Disease ("AD"), Down's Syndrome, Type 2 diabetes mellitus, and mild cognitive impairment (MCI).

AD is a neurodegenerative illness characterized by memory loss and other cognitive deficits. McKhann et al., *Neurology* 34: 939 (1984). It is the most common cause of dementia in the United States. AD can strike persons as young as 40-50 years of age, yet, because the presence of the disease is difficult to determine without dangerous brain biopsy, the time of onset is unknown. The prevalence of AD increases with age, with estimates of the affected population reaching as high as 40-50% by ages 85-90. Evans et al., *JAMA* 262: 2551 (1989); Katzman, *Neurology* 43: 13 (1993).

Neuropathologically, AD is characterized by the presence of neuritic plaques (NP), neurofibrillary tangles (NFT), and neuronal loss, along with a variety of other findings. Mann, *Mech. Ageing Dev.* 31: 213 (1985). Post-mortem slices of brain tissue of victims of AD exhibit the presence of amyloid in the form of proteinaceous extracellular cores of the neuritic plaques that are characteristic of AD. The amyloid cores of these neuritic plaques are composed of a protein called the β-amyloid (Aβ) that is arranged in a predominately beta-pleated sheet configuration.

AD is believed to afflict some 4 million Americans and perhaps 20-30 million people worldwide. AD is recognized as a major public health problem in developed nations. Several therapeutic targets have emerged from the ongoing elucidation of the molecular basis of AD. For example, four cholinesterase inhibitors have been approved for the symptomatic treatment of patients with AD—tacrine (Cognex, Warner-Lambert, Morris Plains, N.J.); donepezil (Aricept, Eisai, Inc., Teaneck, N.J., and Pfizer, Inc., New York, N.Y.); rivagstigmine (Exelon, Novartis, Basel, Switzerland); and galantamine (Reminyl, Janssen, Titusville, N.J.). Potential new AD therapies that are currently being developed involve immunotherapy, secretase inhibitors or anti-inflammatory drugs. However, to date, there are no available drugs proven to modify the course of cognitive decline.

A major hurdle to developing anti-amyloid therapies is exemplified by the following quote from (Hock, C. et al., 2003, *Neuron*, 38:547-554), directed to use of immunotherapy as an anti-amyloid therapy: "[w]e do not know whether brain Aβ-amyloid load was reduced in our study patients; in vivo imaging techniques will be required to answer this question." The ability to quantify amyloid load before treatment and then follow the effects of treatment is critical to the efficient development of this class of drugs. The present invention employs amyloid imaging as a surrogate marker of efficacy for anti-amyloid therapies.

SUMMARY OF THE INVENTION

The present invention is directed to a method of determining the efficacy of therapy in the treatment of amyloidosis, comprising:

(A) administering to a patient in need thereof an effective amount of a compound of the following formula:

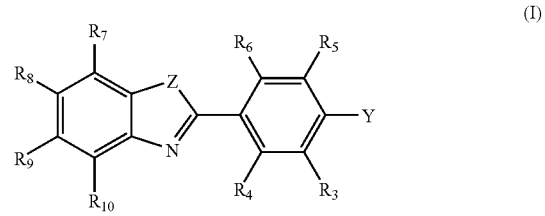

(I)

wherein (i) Z is S, NR', O or C(R')$_2$, such that when Z is C(R')$_2$, the tautomeric form of the heterocyclic ring may form an indole:

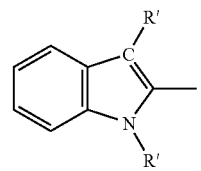

wherein R' is H or a lower alkyl group, (ii) Y is NR$^1$R$^2$, OR$^2$, or SR$^2$, (iii) R$^1$ is selected from the group consisting of H, a lower alkyl group, (CH$_2$)$_n$OR' (wherein n=1, 2, or 3), CF$_3$, CH$_2$—CH$_2$X, CH$_2$—CH$_2$—CH$_2$X (wherein X=F, Cl, Br or I), (C=O)—R', R$_{ph}$, and (CH$_2$)$_n$R$_{ph}$ (wherein n=1, 2, 3, or 4 and R$_{ph}$ represents an unsubstituted or substituted phenyl group with the phenyl substituents being chosen from any of the non-phenyl substituents defined below for R$^3$-R$^{10}$ and R' is H or a lower alkyl group);

(iv) R$^2$ is selected from the group consisting of H, a lower alkyl group, (CH$_2$)$_n$OR' (wherein n=1, 2, or 3), CF$_3$, CH$_2$—CH$_2$X, CH$_2$—CH$_2$—CH$_2$X (wherein X=F, Cl, Br or I), (C=O)—R', R$_{ph}$, and (CH$_2$)$_n$R$_{ph}$ (wherein n=1, 2, 3, or 4 and R$_{ph}$ represents an unsubstituted or substituted phenyl group with the phenyl substituents being chosen from any of the non-phenyl substituents defined below for R$^3$-R$^{10}$ and R' is H or a lower alkyl group);

(v) R$^3$ is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$, CR$_2$'—CR$_2$'—R$_{ph}$ (wherein R$_{ph}$ represents an unsubstituted or substituted phenyl group with the phenyl substituents being chosen from any of the non-phenyl substituents defined for R$^1$-R$^{10}$ and wherein R' is H or a lower alkyl group) and a tri-alkyl tin;

(vi) R$^4$ is selected from the group consisting of H, F, Cl, Br, I, a lower alkyl group, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$—CH$_2$X (wherein X=F, Cl, Br or I), CN, (C=O)—R', N(R')$_2$, NO$_2$, (C=O)N(R')$_2$, O(CO)R', OR', SR', COOR', R$_{ph}$, CR'=CR'—R$_{ph}$, CR$_2$'—CR$_2$'—R$_{ph}$ (wherein R$_{ph}$ represents an unsubstituted or substituted phenyl group with the phenyl substituents being chosen from any of the non-phenyl substituents defined for R$^1$-R$^{10}$ and wherein R$^1$ is H or a lower alkyl group) and a tri-alkyl tin;

(vii) $R^5$ is selected from the group consisting of H, F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, $(C=O)N(R')_2$, $O(CO)R'$, OR', SR', COOR', $R_{ph}$, $CR'=CR'—R_{ph}$, $CR_2'—CR_2'—R_{ph}$ (wherein $R_{ph}$ represents an unsubstituted or substituted phenyl group with the phenyl substituents being chosen from any of the non-phenyl substituents defined for $R^1-R^{10}$ and wherein R' is H or a lower alkyl group) and a tri-alkyl tin;

(viii) $R^6$ is selected from the group consisting of H, F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, $(C=O)N(R')_2$, $O(CO)R'$, OR', SR', COOR', $R_{ph}$, $CR'=CR'—R_{ph}$, $CR_2'—CR_2'—R_{ph}$ (wherein $R_{ph}$ represents an unsubstituted or substituted phenyl group with the phenyl substituents being chosen from any of the non-phenyl substituents defined for $R^1-R^{10}$ and wherein R' is H or a lower alkyl group) and a tri-alkyl tin;

(ix) $R^7$ is selected from the group consisting of H, F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, $(C=O)N(R')_2$, $O(CO)R'$, OR', SR', COOR', $R_{ph}$, $CR'=CR'—R_{ph}$, $CR_2'—CR_2'—R_{ph}$ (wherein $R_{ph}$ represents an unsubstituted or substituted phenyl group with the phenyl substituents being chosen from any of the non-phenyl substituents defined for $R^1-R^{10}$ and wherein R' is H or a lower alkyl group) and a tri-alkyl tin;

(x) $R^8$ is selected from the group consisting of H, F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, $(C=O)N(R')_2$, $O(CO)R'$, OR', SR', COOR', $R_{ph}$, $CR'=CR'—R_{ph}$, $CR_2'—CR_2'—R_{ph}$ (wherein $R_{ph}$ represents an unsubstituted or substituted phenyl group with the phenyl substituents being chosen from any of the non-phenyl substituents defined for $R^1-R^{10}$ and wherein R' is H or a lower alkyl group) and a tri-alkyl tin;

(xi) $R^9$ is selected from the group consisting of H, F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, $(C=O)N(R')_2$, $O(CO)R'$, OR', SR', COOR', $R_{ph}$, $CR'=CR'—R_{ph}$, $CR_2'—CR_2'—R_{ph}$ (wherein $R_{ph}$ represents an unsubstituted or substituted phenyl group with the phenyl substituents being chosen from any of the non-phenyl substituents defined for $R^1-R^{10}$ and wherein R' is H or a lower alkyl group) and a tri-alkyl tin;

(xii) $R^{10}$ is selected from the group consisting of H, F, Cl, Br, I, a lower alkyl group, $(CH_2)_nOR'$ (wherein n=1, 2, or 3), $CF_3$, $CH_2—CH_2X$, $O—CH_2—CH_2X$, $CH_2—CH_2—CH_2X$, $O—CH_2—CH_2—CH_2X$ (wherein X=F, Cl, Br or I), CN, (C=O)—R', $N(R')_2$, $NO_2$, $(C=O)N(R')_2$, $O(CO)R'$, OR', SR', COOR', $R_{ph}$, $CR'=CR'—R_{ph}$, $CR_2'—CR_2'—R_{ph}$ (wherein $R_{ph}$ represents an unsubstituted or substituted phenyl group with the phenyl substituents being chosen from any of the non-phenyl substituents defined for $R^1-R^{10}$ and wherein R' is H or a lower alkyl group) and a tri-alkyl tin;

alternatively, one of $R^3-R^{10}$ may be a chelating group (with or without a chelated metal group) of the form W-L or V-W-L, wherein V is selected from the group consisting of —COO—, —CO—, —$CH_2O$— and —$CH_2NH$—; W is —$(CH_2)_n$ where n=0, 1, 2, 3, 4, or 5; and L is:

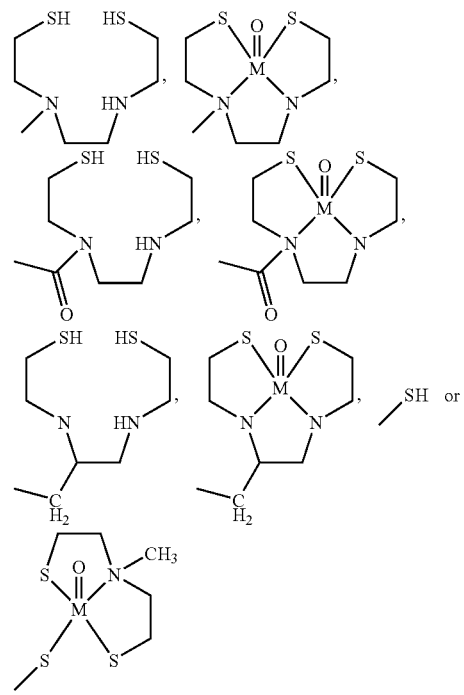

wherein M is selected from the group consisting of Tc and Re;

(B) imaging said patient; then (C) administering to said patient in need thereof at least one anti-amyloid agent;

(D) subsequently administering to said patient in need thereof an effective amount of a compound of formula (I);

(E) imaging said patient; and (F) comparing levels of amyloid deposition in said patient before treatment with said at least one anti-amyloid agent to levels of amyloid deposition in said patient after treatment with said at least one anti-amyloid agent.

In some embodiments, the anti-amyloid agent comprises one or more antibodies against Aβ peptide.

In other embodiments, the anti-amyloid agent comprises one or more inhibitors of β- and/or γ-secretase.

In some embodiments, the anti-amyloid agent comprises a small molecule that binds to Aβ1-42, such as a decoy peptide.

In other embodiments, the amyloidosis is AD.

In some embodiment, the amyloidosis is an amyloid deposition disorder, wherein a preferred embodiment encompasses amyloidosis which is an amyloid plaque deposition disorder.

In some embodiments, the imaging is selected from the group consisting of gamma imaging, magnetic resonance imaging, and magnetic resonance spectroscopy.

In other embodiments, the imaging is done by gamma imaging, and the gamma imaging is PET or SPECT.

In some embodiments, the compound of Formula (I) is:

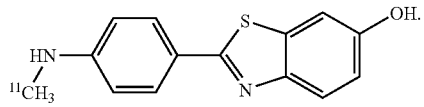

In other embodiments, the compound of Formula (I) contains a $^{11}C$ label.

In some embodiments, the anti-amyloid agent is a peripheral sink agent.

DETAILED DESCRIPTION

Figure 1:
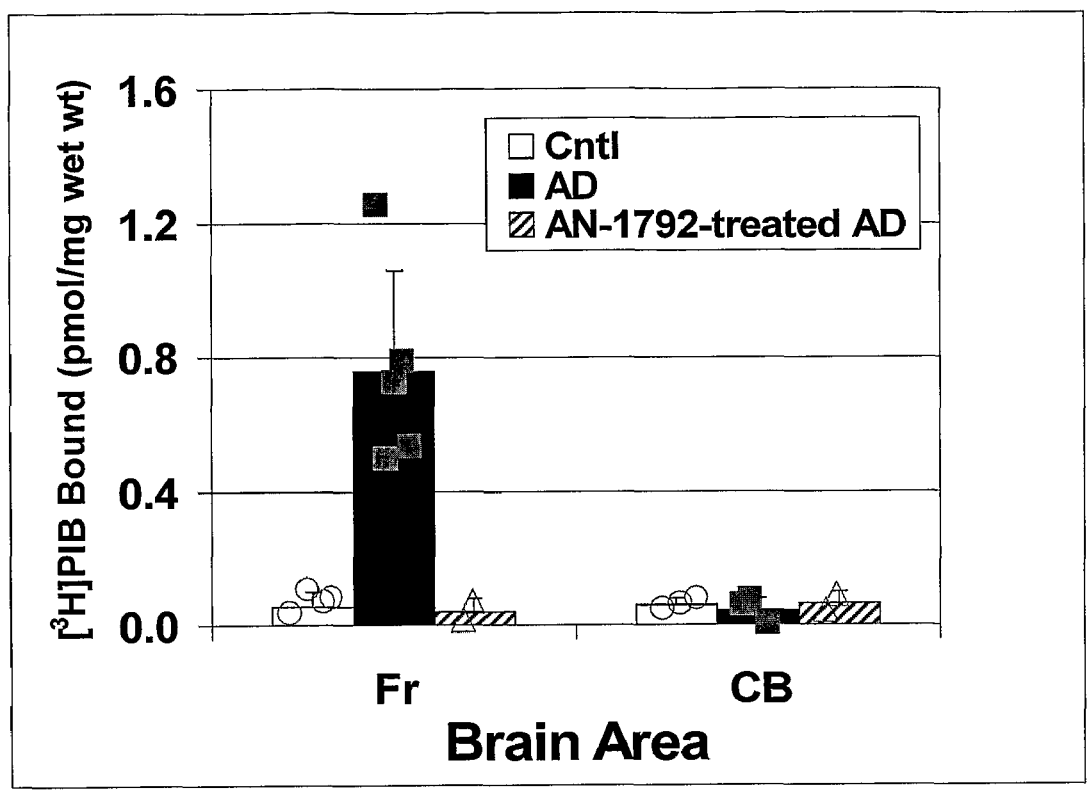
FIG. 1 shows binding of 1 nM {N-methyl-$^3$H}2-[4'-(methylamino)phenyl]6-hydroxy-benzothiazole ("[$^3$H]PIB") to frontal cortex (Fr) and cerebellum (Cb) of control brain (Cntl; n=4; white bars; circles), AD brain (AD; n=5; black bars; squares) and an AN-1792-treated AD case (n=1 repeated×1; hatched bars; triangles). The results indicate that treatment with AN-1792 vaccine decreases the binding of the amyloid tracer, 2-[4'-(methylamino)phenyl]6-hydroxy-benzothiazole ("PIB"), to brain homogenates.

The present invention is directed to a method for determining the efficacy of therapy in the treatment of amyloidosis. The method involves the use of amyloid imaging as a surrogate marker. Surrogate markers are a special type of biomarker that may be used in place of clinical measurements as a clinical endpoint for drug approval purposes. Thus, the methods described herein are useful in drug development trials. For example, the measurement of cholesterol levels is now an accepted surrogate marker of atherosclerosis. In addition, the methods are clinically useful in assisting patient management decisions. In that regard, quantitative evaluations of amyloid burden can improve clinical decisions concerning drug dose or treatment selections. The present invention involves the use of amyloid imaging as a surrogate marker of efficacy for anti-amyloid therapies.

The term "amyloidosis" refers to a disease associated with amyloid deposition, such as Alzheimer's Disease, Down's Syndrome, Type 2 diabetes mellitus, hereditary cerebral hemorrhage amyloidosis (Dutch), amyloid A (reactive), secondary amyloidosis, MCI, familial Mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish)), familial amyloid cardiomyopathy (Danish), isolated cardiac amyloid, systemic senile amyloidoses, AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-I (familial amyloidotic polyneuropathy-Iowa), AApo-A-II (accelerated senescence in mice), fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele, and the condition associated with homozygosity for the apolipoprotein E4 allele or Huntington's disease. The invention encompasses diseases associated with amyloid plaque deposition. Preferably, the disease associated with amyloid deposition is AD.

The present method provides a means of evaluating success of anti-amyloid therapies. In some embodiments, the present method provides a means for evaluating clinical success of anti-amyloid therapies. In some embodiments, the method may be used to evaluate clinical success in mildly impaired subjects with few or no clinical symptoms to follow. The basic method of determining the efficacy of therapy in the treatment of amyloidosis involves:

(A) administering to a patient in need thereof an effective amount of compound of the following formula:

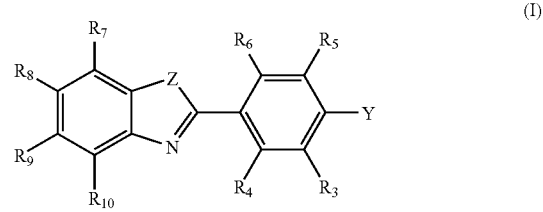

(I)

wherein (i) Z is S, NR', O or C(R')$_2$, such that when Z is C(R')$_2$, the tautomeric form of the heterocyclic ring may form an indole:

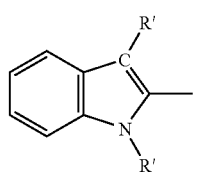

wherein R' is H or a lower alkyl group, (ii) Y is $NR^1R^2$, $OR^2$, or $SR^2$, (iii) $R^1$ is selected from the group consisting of H, a lower alkyl group, $(CH_2)_nOR'$ (wherein n=1, 2, or 3), $CF_3$, $CH_2$—$CH_2X$, $CH_2$—$CH_2$—$CH_2X$ (wherein X=F, Cl, Br or I), (C=O)—R', $R_{ph}$, and $(CH_2)_nR_{ph}$ (wherein n=1, 2, 3, or 4 and $R_{ph}$ represents an unsubstituted or substituted phenyl group with the phenyl substituents being chosen from any of the non-phenyl substituents defined below for $R^3$-$R^{10}$ and R' is H or a lower alkyl group);

(iv) $R^2$ is selected from the group consisting of H, a lower alkyl group, $(CH_2)_nOR'$ (wherein n=1, 2, or 3), $CF_3$, $CH_2$—$CH_2X$, $CH_2$—$CH_2$—$CH_2X$ (wherein X=F, Cl, Br or I), (C=O)—R', $R_{ph}$, and $(CH_2)_nR_{ph}$ (wherein n=1, 2, 3, or 4 and $R_{ph}$ represents an unsubstituted or substituted phenyl group with the phenyl substituents being chosen from any of the non-phenyl substituents defined below for $R^3$-$R^{10}$ and R' is H or a lower alkyl group);]

(v) $R^3$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

(vi) $R^4$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

(vii) $R^5$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

(viii) $R^6$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

(ix) $R^7$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

(x) $R^8$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

(xi) $R^9$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

(xii) $R^{10}$ is selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2$—$CH_2X$ (wherein X=F, Cl, Br or I), CN, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group with the phenyl substituents being chosen from any of the non-phenyl substituents defined for $R^1$-$R^{10}$ and wherein R' is H or a lower alkyl group) and a tri-alkyl tin;

alternatively, one of $R^3$-$R^{10}$ may be a chelating group (with or without a chelated metal group) of the form W-L or V-W-L, wherein V is selected from the group consisting of —COO—, —CO—, —$CH_2O$— and —$CH_2NH$—; W is —$(CH_2)_n$ where n=0, 1, 2, 3, 4, or 5; and L is:

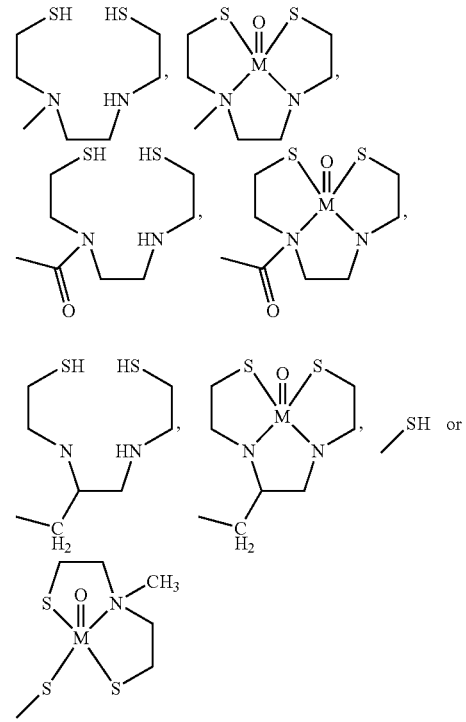

wherein M is selected from the group consisting of Tc and Re;

and radiolabeled derivatives and pharmaceutically acceptable salts thereof, where at least one of the substituent moieties comprises a detectable label;

(B) imaging said patient; then (C) administering to said patient in need thereof at least one anti-amyloid agent;

(D) subsequently administering to said patient in need thereof an effective amount of a compound of formula (I);

(E) imaging said patient; and (F) comparing levels of amyloid deposition in said patient before treatment with at least one anti-amyloid agent to levels of amyloid deposition in said patient after treatment with at least one anti-amyloid agent.

The detectable label includes any atom or moiety which can be detected using an imaging technique known to those skilled in the art. Typically, the detectable label is selected from the group consisting of $^3H$, $^{131}I$, $^{125}I$, $^{123}I$, $^{76}Br$, $^{75}Br$, $^{18}F$, $CH_2$—$CH_2$—$X^*$, $O$—$CH_2$—$CH_2$—$X^*$, $CH_2$—$CH_2$—$CH_2$—$X^*$, $O$—$CH_2$—$CH_2$—$CH_2$—$X^*$ (wherein $X^*=^{131}I$, $^{123}I$, $^{76}Br$, $^{75}Br$ or $^{18}F$), $^{19}F$, $^{125}I$, a carbon-containing substituent selected from the group consisting of lower alkyl, $(CH_2)_nOR'$, $CF_3$, $CH_2$—$CH_2X$, $O$—$CH_2$—$CH_2X$, $CH_2$—$CH_2$—$CH_2X$, $O$—$CH_2$—$CH_2$—$CH_2X$ (wherein $X=F$, $Cl$, $Br$ or $I$), $CN$, $(C=O)$—$R'$, $(C=O)N(R')_2$, $O(CO)R'$, $COOR'$, $CR'=CR'$—$R_{ph}$ and $CR_2'$—$CR_2'$—$R_{ph}$ wherein at least one carbon is $^{11}C$, $^{13}C$ or $^{14}C$ and a chelating group (with chelated metal group) of the form W-L* or V-W-L*, wherein V is selected from the group consisting of —COO—, —CO—, —$CH_2O$— and —$CH_2NH$—; W is —$(CH_2)_n$ where n=0, 1, 2, 3, 4, or 5; and L* is:

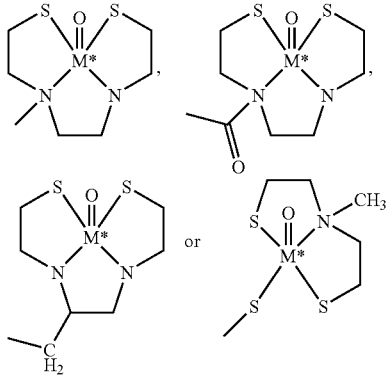

wherein M* is $^{99m}Tc$. In a preferred embodiment, the detectable label is a radiolabel.

In a preferred embodiment, the detectable label is a radiolabel.

Amyloid Probes

The amyloid probe of the present invention is any compound of formula (I), described above.

In some embodiments, the amyloid probe is a compound of formula (II)

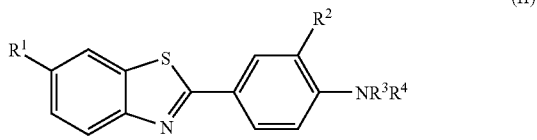

(II)

or a radiolabeled derivative, pharmaceutically acceptable salt, hydrate, solvate or prodrug of the compound, wherein:

$R^1$ is hydrogen, —OH, —$NO_2$, —CN, —COOR, —$OCH_2OR$, $C_1$-$C_6$ alkyl, $C_2$-$C_6$ alkenyl, $C_2$-$C_6$ alkynyl, $C_1$-$C_6$ alkoxy or halo;

R is $C_1$-$C_6$ alkyl;

$R^2$ is hydrogen or halo;

$R^3$ is hydrogen, $C_1$-$C_6$ alkyl, $C_2$-$C_6$ alkenyl or $C_2$-$C_6$ alkynyl; and $R^4$ is hydrogen, $C_1$-$C_6$ alkyl, $C_2$-$C_6$ alkenyl or $C_2$-$C_6$ alkynyl, wherein the alkyl, alkenyl or alkynyl comprises a radioactive carbon or is substituted with a radioactive halo when $R^2$ is hydrogen or a non-radioactive halo;

provided that when $R^1$ is hydrogen or —OH, $R^2$ is hydrogen and $R^4$ is —$^{11}CH_3$, then $R^3$ is $C_2$-$C_6$ alkyl, $C_2$-$C_6$ alkenyl or $C_2$-$C_6$ alkynyl; and further provided that when $R^1$ is hydrogen, $R^2$ hydrogen and $R^4$ is —$(CH_2)_3$$^{18}F$, then $R^3$ is $C_2$-$C_6$ alkyl, $C_2$-$C_6$ alkenyl or $C_2$-$C_6$ alkynyl, where at least one of the substituent moieties comprises a detectable label.

In one embodiment, $R^2$ in the compounds of formula (II) contains a radioactive halo.

"Alkyl" refers to a saturated straight or branched chain hydrocarbon radical. Examples include without limitation methyl, ethyl, propyl, iso-propyl, butyl, iso-butyl, tert-butyl, n-pentyl and n-hexyl. The term "lower alkyl" refers to $C_1$-$C_6$ alkyl.

"Alkenyl" refers to an unsaturated straight or branched chain hydrocarbon radical comprising at least one carbon to carbon double bond. Examples include without limitation ethenyl, propenyl, iso-propenyl, butenyl, iso-butenyl, tert-butenyl, n-pentenyl and n-hexenyl.

"Alkynyl" refers to an unsaturated straight or branched chain hydrocarbon radical comprising at least one carbon to carbon triple bond. Examples include without limitation ethynyl, propynyl, iso-propynyl, butynyl, iso-butynyl, tert-butynyl, pentynyl and hexynyl.

"Alkoxy" refers to an alkyl group bonded through an oxygen linkage.

"Halo" refers to a fluoro, chloro, bromo or iodo radical.

"Radioactive halo" refers to a radioactive halo, i.e. radiofluoro, radiochloro, radiobromo or radioiodo.

In another embodiment, the thioflavin compound of formula (I) is selected from the group consisting of structures 1-45 or a radiolabeled derivative thereof:

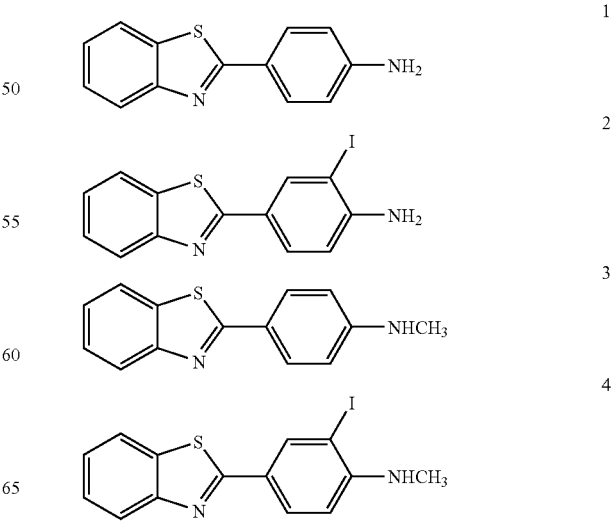

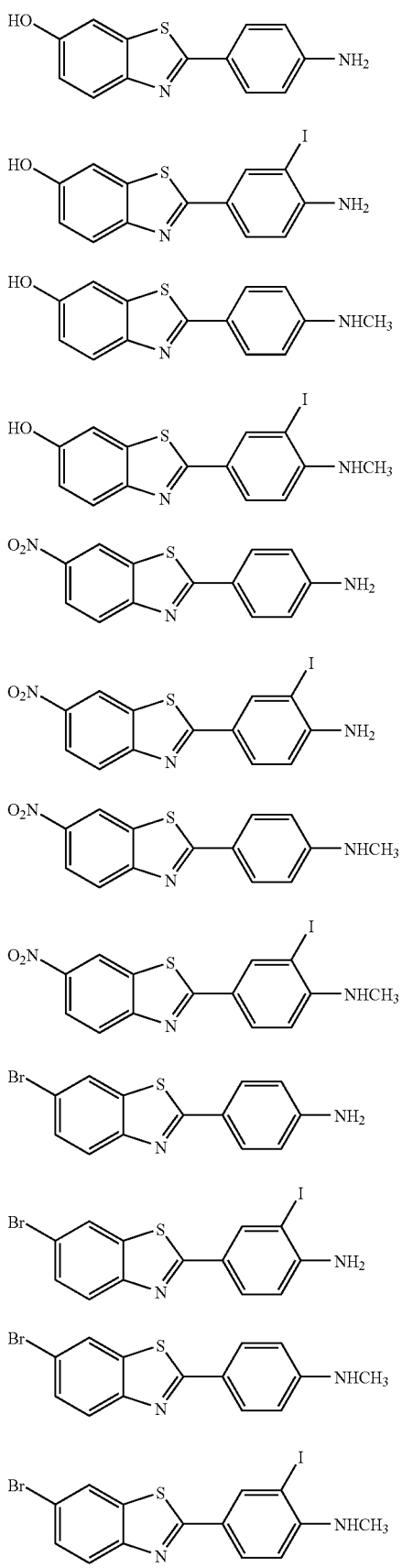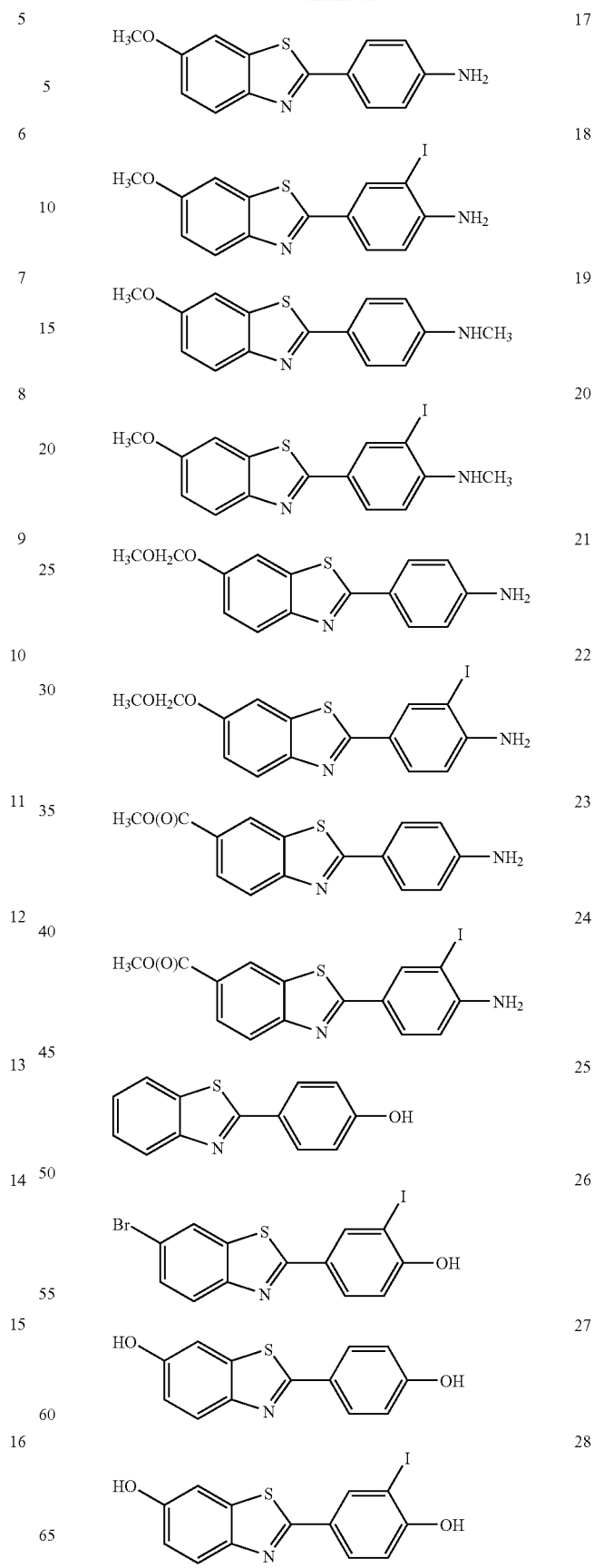

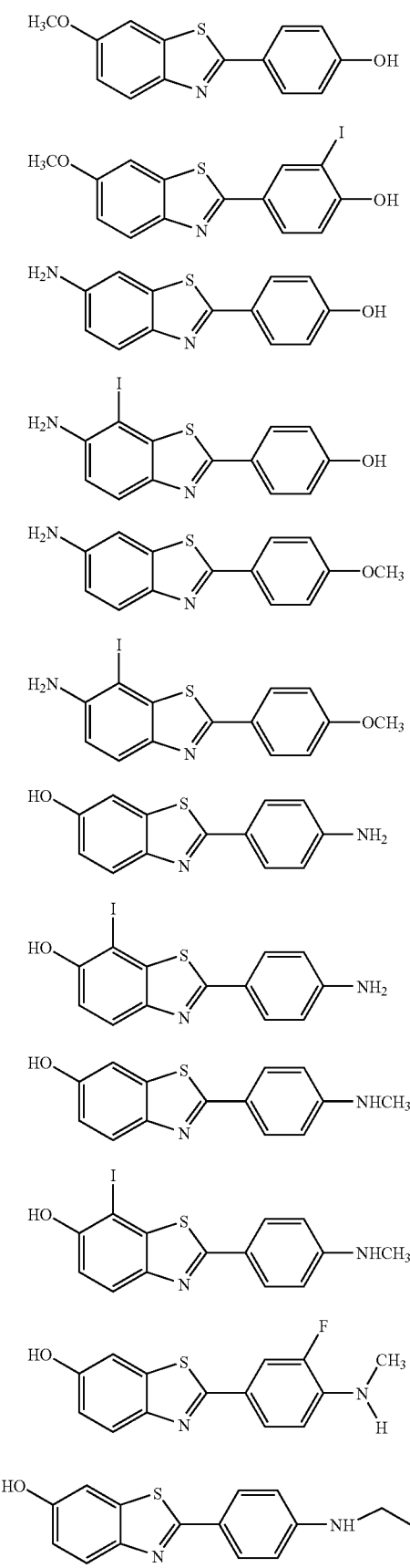
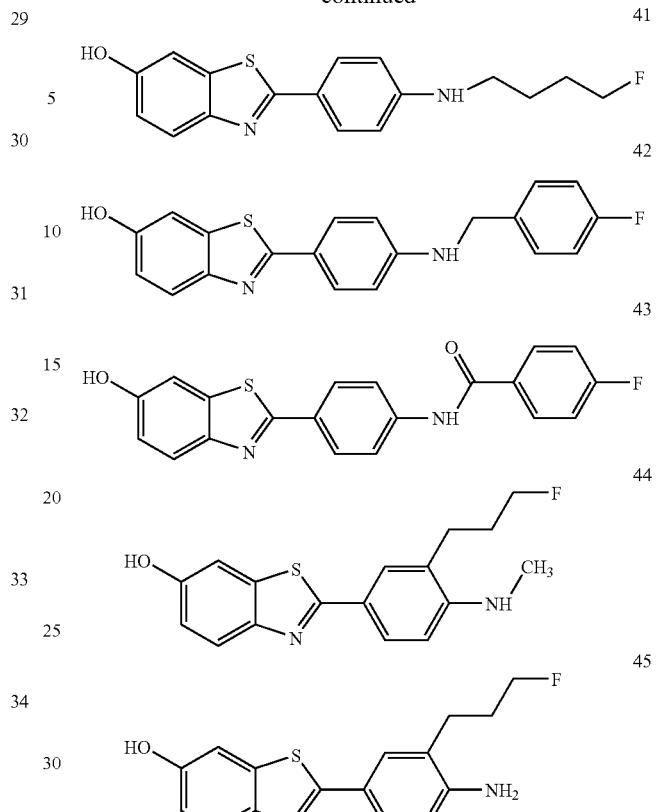

In preferred embodiments, the amyloid probe is {N-methyl-$^{11}$C}2-[4'-(methylamino)phenyl]6-hydroxybenzothiazole ("[$^{11}$C]PIB") or {N-methyl-3H}2-[4'-(methylamino)phenyl]6-hydroxybenzothiazole ("[$^{3}$H]PIB").

"Effective amount" refers to the amount required to produce a desired effect. Examples of an "effective amount" include amounts that enable detecting and imaging of amyloid deposit(s) in vivo or in vitro, that yield acceptable toxicity and bioavailability levels for pharmaceutical use, and/or prevent cell degeneration and toxicity associated with fibril formation.

Compounds of formulas (I) and (II), also referred to herein as "thioflavin compounds," "thioflavin derivatives," or "amyloid probes," have each of the following characteristics: (1) specific binding to synthetic Aβ in vitro and (2) ability to cross a non-compromised blood brain barrier in vivo.

The thioflavin compounds and radiolabeled derivatives thereof of formulas (I) and (II) and structures 1-45 cross the blood brain barrier in vivo and bind to Aβ deposited in neuritic (but not diffuse) plaques, to Aβ deposited in cerebrovascular amyloid, and to the amyloid consisting of the protein deposited in NFT. The present compounds are non-quaternary amine derivatives of Thioflavin S and T which are known to stain amyloid in tissue sections and bind to synthetic Aβ in vitro. Kelenyi *J. Histochem. Cytochem.* 15: 172 (1967); Burns et al. *J. Path. Bact.* 94:337 (1967); Guntern et al. *Experientia* 48: 8 (1992); LeVine *Meth. Enzymol.* 309: 274 (1999).

The method of this invention determines the presence and location of amyloid deposits in an organ or body area, preferably brain, of a patient. The present method comprises administration of a detectable quantity of an amyloid probe of formulas (I) or (II) and structures 1-45. In some embodiments, the amyloid probe is chosen from structures 1-45, as shown above. An amyloid probe may be administered to a patient as a pharmaceutical composition or a pharmaceutically acceptable water-soluble salt thereof.

"Pharmaceutically acceptable salt" refers to an acid or base salt of the inventive compound, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quaternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

Generally, the dosage of the detectably labeled thioflavin derivative will vary depending on considerations such as age, condition, sex, and extent of disease in the patient, contraindications, if any, concomitant therapies and other variables, to be adjusted by a physician skilled in the art. Dosage can vary from 0.001 µg/kg to 10 µg/kg, preferably 0.01 µg/kg to 1.0 µg/kg.

Administration to the subject may be local or systemic and accomplished intravenously, intraarterially, intrathecally (via the spinal fluid) or the like. Administration may also be intradermal or intracavitary, depending upon the body site under examination. After a sufficient time has elapsed for the compound to bind with the amyloid, for example 30 minutes to 48 hours, the area of the subject under investigation is examined by routine imaging techniques such as MRS/MRI, SPECT, planar scintillation imaging, PET, and any emerging imaging techniques, as well. The exact protocol will necessarily vary depending upon factors specific to the patient, as noted above, and depending upon the body site under examination, method of administration and type of label used; the determination of specific procedures would be routine to the skilled artisan. For brain imaging, preferably, the amount (total or specific binding) of the bound radioactively labeled thioflavin derivative or analogue of the present invention is measured and compared (as a ratio) with the amount of labeled thioflavin derivative bound to the cerebellum of the patient. This ratio is then compared to the same ratio in age-matched normal brain.

The amyloid probes of the present invention are advantageously administered in the form of injectable compositions, but may also be formulated into well known drug delivery systems (e.g., oral, rectal, parenteral (intravenous, intramuscular, or subcutaneous), intracisternal, intravaginal, intraperitoneal, local (powders, ointments or drops), or as a buccal or nasal spray). A typical composition for such purpose comprises a pharmaceutically acceptable carrier. For instance, the composition may contain about 10 mg of human serum albumin and from about 0.5 to 500 micrograms of the labeled thioflavin derivative per milliliter of phosphate buffer containing NaCl. Other pharmaceutically acceptable carriers include aqueous solutions, non-toxic excipients, including salts, preservatives, buffers and the like, as described, for instance, in REMINGTON'S PHARMACEUTICAL SCIENCES, 15th Ed. Easton: Mack Publishing Co. pp. 1405-1412 and 1461-1487 (1975) and THE NATIONAL FORMULARY XIV., 14th Ed. Washington: American Pharmaceutical Association (1975), the contents of which are hereby incorporated by reference.

Particularly preferred amyloid probes of the present invention are those that, in addition to specifically binding amyloid in vivo and capable of crossing the blood brain barrier, are also non-toxic at appropriate dosage levels and have a satisfactory duration of effect.

According to the present invention, a pharmaceutical composition comprising an amyloid probe of formula (I) or formula (II) or one of the structures 1-45, is administered to subjects in whom amyloid or amyloid fibril formation are anticipated, e.g., patients clinically diagnosed with Alzheimer's disease or another disease associated with amyloid deposition.

Examples of non-aqueous solvents are propylene glycol, polyethylene glycol, vegetable oil and injectable organic esters such as ethyl oleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. See, Goodman and Gilman's THE PHARMACOLOGICAL BASIS FOR THERAPEUTICS (7th Ed.).

Imaging

The invention employs amyloid probes which, in conjunction with non-invasive neuroimaging techniques such as magnetic resonance spectroscopy (MRS) or imaging (MRI), or gamma imaging such as positron emission tomography (PET) or single-photon emission computed tomography (SPECT), are used to quantify amyloid deposition in vivo. The method involves imaging a patient to establish a baseline of amyloid deposition. The term "baseline" refers to the amount and distribution of a patient's amyloid deposition prior to initiation of the anti-amyloid therapy. The method further involves at least one imaging session of a patient following administration of an anti-amyloid therapy. The present method may involve imaging a patient before and after treatment with at least one anti-amyloid agent. Imaging may be performed at any time during the treatment.

The term "in vivo imaging" refers to any method which permits the detection of a labeled thioflavin derivative of formulas (I) or (II) or one of structures 1-45. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. A "subject" is a mammal, preferably a human, and most preferably a human suspected of having a disease associated with amyloid deposition, such as AD and/or dementia. The term "subject" and "patient" are used interchangeably herein.

For purposes of in vivo imaging, the type of detection instrument available is a major factor in selecting a given label. For instance, radioactive isotopes and $^{18}$F are particularly suitable for in vivo imaging in the methods of the present invention. The type of instrument used will guide the selection of the radionuclide or stable isotope. For instance, the radionuclide chosen must have a type of decay detectable by a given type of instrument. Another consideration relates to the half-life of the radionuclide. The half-life should be long enough so that it is still detectable at the time of maximum uptake by the target, but short enough so that the host does not sustain deleterious radiation. The radiolabeled compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range. For PET detection, the radiolabel will be a positron-emitting radionuclide such as $^{18}$F which will annihilate to form two 511 keV gamma rays which will be detected by the PET camera.

In the present invention, amyloid binding compounds/probes, which are useful for in vivo imaging and quantification of amyloid deposition, are administered to a patient. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the thioflavin derivatives may be labeled with $^{18}$F or $^{13}$C for MRS/MRI by general organic chemistry techniques known to the art. See, e.g., March, J. ADVANCED ORGANIC CHEMISTRY: REACTIONS, MECHANISMS, AND STRUCTURE (3rd Edition, 1985), the contents of which are hereby incorporated by reference. The thioflavin derivatives also may be radiolabeled with $^{18}$F, $^{11}$C, $^{75}$Br, or $^{76}$Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The thioflavin derivatives also may be radiolabeled with $^{123}$I for SPECT by any of several techniques known to the art. See, e.g., Kulkarni, *Int. J. Rad. Appl. & Inst.* (Part B) 18: 647 (1991), the contents of which are hereby incorporated by reference. In addition, the thioflavin derivatives may be labeled with any suitable radioactive iodine isotope, such as, but not limited to $^{131}$I, $^{125}$I, or $^{123}$I, by iodination of a diazotized amino derivative directly via a diazonium iodide, see Greenbaum, F. *Am. J. Pharm.* 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art. See, Satyamurthy and Barrio *J. Org. Chem.* 48: 4394 (1983), Goodman et al., *J. Org. Chem.* 49: 2322 (1984), and Mathis et al., *J. Labell. Comp. and Radiopharm.* 1994: 905; Chumpradit et al., *J. Med. Chem.* 34: 877 (1991); Zhuang et al., *J. Med. Chem.* 37: 1406 (1994); Chumpradit et al., *J. Med. Chem.* 37: 4245 (1994). For example, a stable triazene or tri-alkyl tin derivative of thioflavin or its analogues is reacted with a halogenating agent containing $^{131}$I, $^{125}$I, $^{123}$I, $^{76}$Br, $^{75}$Br, $^{18}$F or $^{19}$F. Thus, the stable tri-alkyl tin derivatives of thioflavin and its analogues are novel precursors useful for the synthesis of many of the radiolabeled compounds within the present invention. As such, these tri-alkyl tin derivatives are one embodiment of this invention.

The thioflavin derivatives also may be radiolabeled with known metal radiolabels, such as Technetium-99m ($^{99m}$Tc). Modification of the substituents to introduce ligands that bind such metal ions can be effected without undue experimentation by one of ordinary skill in the radiolabeling art. The metal radiolabeled thioflavin derivative can then be used to detect amyloid deposits. Preparing radiolabeled derivatives of Tc$^{99m}$ is well known in the art. See, for example, Zhuang et al., "Neutral and stereospecific Tc-99m complexes: [99 mTc] N-benzyl-3,4-di-(N-2-mercaptoethyl)-amino-pyrrolidines (P-BAT)" *Nuclear Medicine & Biology* 26(2):217-24, (1999); Oya et al., "Small and neutral Tc(v)O BAT, bisaminoethanethiol (N2S2) complexes for developing new brain imaging agents" *Nuclear Medicine & Biology* 25(2):135-40, (1998); and Hom et al., "Technetium-99m-labeled receptor-specific small-molecule radiopharmaceuticals: recent developments and encouraging results" *Nuclear Medicine & Biology* 24(6):485-98, (1997).

The methods of the present invention may use isotopes detectable by nuclear magnetic resonance spectroscopy for purposes of in vivo imaging and spectroscopy. Elements particularly useful in magnetic resonance spectroscopy include $^{18}$F and $^{13}$C.

Suitable radioisotopes for purposes of this invention include beta-emitters, gamma-emitters, positron-emitters, and x-ray emitters. These radioisotopes include $^{131}$I, $^{123}$I, $^{18}$F, $^{11}$C, $^{75}$Br, and $^{76}$Br. Suitable stable isotopes for use in Magnetic Resonance Imaging (MRI) or Spectroscopy (MRS), according to this invention, include $^{18}$F and $^{13}$C. Suitable radioisotopes for in vitro quantification of amyloid in homogenates of biopsy or post-mortem tissue include $^{125}$I, $^{14}$C, and $^{3}$H. The preferred radiolabels are $^{11}$C or $^{18}$F for use in PET in vivo imaging, $^{123}$I for use in SPECT imaging, $^{19}$F for MRS/MRI, and $^{3}$H or $^{14}$C for in vitro studies. However, any conventional method for visualizing diagnostic probes can be utilized in accordance with this invention.

According to an aspect of the invention which relates to a method of detecting amyloid deposits in biopsy tissue, the method involves incubating formalin-fixed tissue with a solution of a thioflavin amyloid binding compound chosen from compounds of formulas (I) and (II) or structures 1-45, described above. Preferably, the solution is 25-100% ethanol, (with the remainder being water) saturated with a thioflavin amyloid binding compound of formulas (I) or (II) or structures 1-45 according to the invention. Upon incubation, the compound stains or labels the amyloid deposit in the tissue, and the stained or labeled deposit can be detected or visualized by any standard method. Such detection means include microscopic techniques such as bright-field, fluorescence, laser-confocal and cross-polarization microscopy.

The method of quantifying the amount of amyloid in biopsy tissue involves incubating a labeled derivative of thioflavin according to the present invention, or a water-soluble, non-toxic salt thereof, with homogenate of biopsy or post-mortem tissue. The tissue is obtained and homogenized by methods well known in the art. The preferred label is a radiolabel, although other labels such as enzymes, chemiluminescent and immunofluorescent compounds are well known to skilled artisans. The preferred radiolabel is $^{125}$I, $^{14}$C or $^{3}$H which is contained in a substituent substituted on one of the compounds of formulas (I) or (II) or structures 1-45. Tissue containing amyloid deposits will bind to the labeled derivatives of the thioflavin amyloid binding compounds of the present invention. The bound tissue is then separated from the unbound tissue by any mechanism known to the skilled artisan, such as filtering. The bound tissue can then be quantified through any means known to the skilled artisan. The units of tissue-bound radiolabeled thioflavin derivative are then converted to units of micrograms of amyloid per 100 mg of tissue by comparison to a standard curve generated by incubating known amounts of amyloid with the radiolabeled thioflavin derivative.

The ability of the compound of formulas (I) and (II) or structures 1-45 to specifically bind to amyloid plaques over neurofibrially tangles is particularly true at concentrations less than 10 nM, which includes the in vivo concentration range of PET radiotraces. At these low concentrations, in homogenates of brain tissue which contain only tangles and no plaques, significant binding does not result when compared to control brain tissue containing neither plaques nor tangles. However, incubation of homogenates of brain tissue which contains mainly plaques and some tangles with radiolabeled compounds of Formula (I) or (II) or structures 1-45, results in a significant increase in binding when compared to control tissue without plaques or tangles. This data suggests the advantage that these compounds are specific for Aβ deposits at concentrations less than 10 nM. These low concentrations are then detectable with PET studies, making PET detection using radiolabeled compounds of Formula (I) or Formula (II) or structures 1-45 which are specific for Aβ deposits possible. The use of such compounds permits PET detection in Aβ deposits such as those found in plaques and cerebrovascular amyloid. Since it has been reported that Aβ levels in the frontal cortex are increased prior to tangle formation, this would suggest that radiolabeled compounds of Formula (I) or Formula (II) or structures 1-45, used as PET tracers, would be specific for the earliest changes in AD cortex. Naslund et al. JAMA 283:1571 (2000).

Anti-Amyloid Therapies

The present method for determining the efficacy of therapy in the treatment of amyloidosis involves administering to a patient in need thereof a compound of formulas (I) or (II) or structure 1-45 and imaging the patient, and, after said imaging, administering at least one anti-amyloid agent/anti-amyloid therapy said patient. The amount administered, the route of administration, and the duration of therapy are determined by one skilled in the art based on age, weight, and condition of the patient. Such determinations are within the purview of the skilled practitioner. Suitable amounts include, but are not limited to, 0.01 to 100 mg/kg. Suitable routes of administration include, but are not limited to oral, subcutaneous and intravenous. Suitable durations of therapy include, but are not limited to one single dose to four doses per day given indefinitely. Suitable times to image include, but are not limited to immediately after the first dose to ten years after the most recent dose. Preferred times to image would be between 7 days and 6 months after the most recent dose.

An "Anti-amyloid agent" or an "anti-amyloid therapy" is any agent or combination of agents that treat or prevent amyloidosis. Examples of diseases associated with amyloid deposition, amyloidosis, include Alzheimer's Disease, Down's Syndrome, Type 2 diabetes mellitus, hereditary cerebral hemorrhage amyloidosis (Dutch), amyloid A (reactive), secondary amyloidosis, MCI, familial Mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish)), familial amyloid cardiomyopathy (Danish), isolated cardiac amyloid, systemic senile amyloidoses, AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-I (familial amyloidotic polyneuropathy-Iowa), AApo-A-II (accelerated senescence in mice), fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele, and the condition associated with homozygosity for the apolipoprotein E4 allele or Huntington's disease. The invention encompasses diseases associated with amyloid plaque deposition. Preferably, the disease associated with amyloid deposition is AD.

The term "therapy" includes treating and/or preventing disease.

"Treating" refers to:

(i) preventing a disease, disorder or condition from occurring in an animal that may be predisposed to the disease, disorder and/or condition but has not yet been diagnosed as having it;

(ii) inhibiting the disease, disorder or condition, i.e., arresting its development; and/or (iii) relieving the disease, disorder or condition, i.e., causing regression of the disease, disorder and/or condition.

The term "treating" or "treatment" does not necessarily mean total cure. Any alleviation of any undesired symptom or pathological effect of the disease to any extent or the slowing down of the progress of the disease can be considered treatment. Furthermore, treatment may include acts which may worsen the patient's overall feeling of well being or appearance. For example, the administration of chemotherapy in cancer patients which may leave the patients feeling "sicker" is still considered treatment.

The term "preventing" refers to decreasing the probability that an organism contracts or develops a disease associated with amyloid deposition. The term "preventing" preferably refers to reducing the percentage of individuals who develop the disease relative to a control group that does not undergo administration of an anti-amyloid agent.

The present invention is directed to amyloid imaging serving as a surrogate marker of efficacy for anti-amyloid therapy. Administration of an amyloid probe to establish a baseline of amyloid deposition and subsequent imaging of a patient both before and after treatment of the patient with an anti-amyloid agent allows for determination of the efficacy of the anti-amyloid therapy. The present method can be used to determine the efficacy of any anti-amyloid treatment because an amyloid probe can be administered, and the patient can be imaged, before and after any anti-amyloid therapy. The present method contemplates determining anti-amyloid therapies which are ineffective for treating diseases associated with amyloid deposition, as well as anti-amyloid therapies which are effective for treating diseases associated with amyloid deposition. A person of ordinary skill in the art can determine the conditions and dosing of the anti-amyloid therapy according to appropriate protocols. Therefore, the present invention contemplates determining the efficacy of anti-amyloid therapies that are now known, as well as therapies that are yet to be discovered. Exemplary non-limiting anti-amyloid therapies are described below.

In some embodiments, the efficacy of acetylcholinesterase inhibitors in the treatment of amyloidosis is determined by the present method. Acetylcholinesterase therapy is based on studies of degeneration patterns in AD which identified substantial decreases among groups of neurons in the basal forebrain. These cells all used the transmitter acetylcholine, and their loss meant that less acetylcholine was being released at their former terminals in the cortex. Several drugs, such as tacrine, donepezil, rivastigmine and galantamine have been developed based on these findings, and are hypothesized to work by inhibiting the enzyme acetylcholinesterase (Ingram, V., American Scientist, 2003, 91(4):312-321).

In other embodiments, the efficacy of anti-amyloid therapy targeting enzymes responsible for formation of noxious fragments of amyloid precursor protein (APP) in the treatment of amyloidosis is determined by the present method. In some embodiments, the noxious fragments of the amyloid precursor protein (APP) is misfolded Aβ peptide. For example, the overproduction of Aβ1-42 fragment is considered by some scientists to be a root cause of AD. The Aβ1-42 fragment is formed by cleavage of APP by the β-secretase enzyme (BACE1) (which produces the amino terminus) and the γ-secretase enzyme (which cleaves the carboxyl terminus of APP). Inhibitors of these secretase enzymes may be used as anti-amyloid therapies (Ingram, V., American Scientist, 2003, 91(4):312-321).

In some embodiments, the efficacy of immunotherapeutic strategies in the treatment of amyloidosis can be determined by the present method. Immunotherapy works by using the patient's immune system to locate and destroy amyloid plaques and many immunotherapy strategies are being actively pursued by scientists. The immunotherapeutic strategies can be either passive or active. For example, in active immunotherapy, a patient may receive an injection or nasal-spray application of the Aβ peptide, leading to an anti-amyloid immune response. Passive immunotherapy, on the other hand, might involve bypassing the beta amyloid protein, using instead antiserum that has already been produced in response to beta amyloid. Immunotherapy, involving antibodies against Aβ peptide, has been studied for the treatment of AD. For example, AN-1792 is a preparation of preaggregated synthetic amyloid-beta (Aβ; 1-42 length) along with QS-21 adjuvant (Hock, C. et al., 2003, *Neuron*, 38:547-554). Approximately 300 AD patients have been treated with this preparation prior to suspension of the clinical trial due to side effects (Birmingham, K. and Frantz, S., 2002, *Nature Medicine*, 8:199-200).

In other embodiments, the efficacy of neuroprotective strategies in the treatment of amyloidosis is determined by the present method. For example, many clinicians recommend that patients take high doses (1000-2000 IU/day) of vitamin E. Other types of neuroprotective strategies that have been suggested for the treatment of amyloidosis are high doses of vitamin C, calcium channel modulators, free-radical scavengers, and metal ion chelators (Selkoe, et al., Annu. Rev. Pharmacol. Toxicol., 2003, 43:545-84).

In some embodiments, the efficacy of anti-inflammatory drugs (NSAIDs) strategies in the treatment of amyloidosis is determined by the present method. Treatments involving NSAIDs are based on evidence that a cellular inflammatory response in the cortex is elicited by the progressive accumulation of Aβ peptide. Exemplary anti-inflammatory drugs are prednisone, nonspecific cyclooxygenase inhibitors, and cyclooxygenase-2 inhibitors. (Clark, M., et al., Annals of Internal Medicine, 2003, 138(5):400-410; and Hardy, John, Annu. Rev. Med., 2004, 55:15-25).

In some embodiments, the efficacy of cholesterol-lowering therapies including, but not limited to, the 3-hydroxy-3-methylglutaryl coenzyme A reductase inhibitors (statins) is determined by the present method. Treatments involving cholesterol-lowering drugs (such as statins) are based on epidemiological evidence that patients treated with statins have a lower incidence of AD and that statins can alter the metabolism of Aβ to decrease Aβ levels (Wolozin, B (2002) Cholesterol and Alzheimer's disease. Biochemical Society Transactions. 30:525-529). Exemplary cholesterol-lowering statin drugs include lovastatin, pravastatin, rosuvastatin, fluvastatin, atorvastatin and simvastatin. Other cholesterol-lowering drugs include niacin, cholestyramine, fenofibrate, colesevelam and ezetimibe.

In other embodiments, the efficacy of small molecules that eliminate the neurotoxicity of the aggregated Aβ1-42 in the treatment of amyloidosis is determined by the present method. Such a drug, preferably administered early in disease progression, would "detoxify" the gradually accumulating Aβ peptide before any permanent damage is inflicted on the neurons. (Clark, M., et al., Annals of Internal Medicine, 2003, 138(5):400-410)

In some embodiments, the efficacy of "decoy peptides" in the treatment of amyloidosis is determined by the present method. Decoy peptides are small molecules that bind to the aggregating Aβ1-42 peptide and force it to assume a nontoxic structure. Exemplary decoy peptides are small peptides (5, 6 or 9 amino acids long), selected from large libraries of protein fragments by their ability to form a tight association with tagged Aβ1-42. (Clark, M., et al., Annals of Internal Medicine, 2003, 138(5):400-410).

In other embodiments, the efficacy of cholesterol homeostasis modulation in the treatment of amyloidosis is determined by the present method. Chronic use of cholesterol-lowering drugs has recently been associated with a lower incidence of AD. Concurrently, high-cholesterol diets have been shown to increase Aβ pathology in animals, and cholesterol-lowering drugs have been shown to reduce pathology in APP transgenic mice. Clinical trials are underway to study the effect of cholesterol homeostasis modulation in the treatment of AD. (Hardy, John, Annu. Rev. Med., 2004, 55:15-25)

Certain antibodies such as the one termed m266 (DeMattos, R B, Bales, K R, Cummins, D J, Dodart, J C, Paul, S M, Holtzman, D M (2001) "Peripheral anti-A beta antibody alters CNS and plasma A beta clearance and decreases brain A beta burden in a mouse model of Alzheimer's disease." Proc. Natl. Acad. Sci. USA 98:8850-8855) or molecules other than antibodies (Matsuoka, Y, Saito, M, LaFrancois, J, Saito, M, Gaynor, K, Olm, V, Wang, L, Casey, E, Lu, Y, Shiratori, C, Lemere, C, Duff, K (2001) "Novel therapeutic approach for the treatment of Alzheimer's disease by peripheral administration of agents with an affinity to beta-amyloid." Journal of Neuroscience. 23:29-33) are believed to lower brain amyloid by binding to Aβ peptides in the blood, thereby creating a "peripheral sink" and shifting the equilibrium of Aβ from the brain to the blood, where it can be cleared from the body. Such agents are referred to herein as "peripheral sink agents."

Evaluating the Efficacy of the Anti-Amyloid Therapy

The present method for determining the efficacy of therapy in the treatment of amyloidosis involves administering to a patient in need thereof a compound of formulas (I) or (II) or structure 1-45 and imaging the patient. After said imaging, at least one anti-amyloid agent is administered to said patient. Then, an effective amount of a compound of formulas (I) or (II) or structure 1-45 is administered to the patient and the patient is imaged again. Finally, baseline levels of amyloid deposition in the patient before treatment with the anti-amyloid agent are compared with levels of amyloid deposition in the patient following treatment with the anti-amyloid agent. Such a comparison is within the preview of a skilled practitioner.

In some embodiments, the levels of amyloid deposition in the patient before treatment with the anti-amyloid agent will be higher than the levels of amyloid deposition in the patient following treatment with the anti-amyloid agent. Such a result indicates that the anti-amyloid agent/anti-amyloid therapy is effective in the treatment of diseases associated with amyloid deposition.

For example, AN-1792 is a preparation of preaggregated synthetic amyloid-beta (Aβ; 1-42 length) along with QS-21 adjuvant. Approximately 300 AD patients have been treated with this preparation prior to suspension of the clinical trial due to side effects (Birmingham, K. and Frantz, S., 2002, *Nature Medicine*, 8:199-200). Despite this set back, optimism over this approach has been raised by two findings. First, in the only autopsy report yet published regarding an AN-1792-treated AD patient, there were several unusual findings including: (i) extensive areas of neocortex with very few Aβ plaques; (ii) areas of cortex that were devoid of Aβ plaques contained densities of tangles, neuropil threads and cerebral amyloid angiopathy (CAA) similar to unimmunized AD, but lacked plaque-associated dystrophic neurites and astrocyte clusters; (iii) in some regions devoid of plaques, Aβ-immunoreactivity was associated with microglia (Nicoll, J. et al., 2003, *Nature Medicine*, 9:448-452). Second, in a small subset of 30 AN-1792-treated patients, those patients who generated antibodies against Aβ, as determined by a tissue amyloid plaque immunoreactivity (TAPIR) assay showed significantly slower rates of decline of cognitive functions and activities of daily living, as indicated by the Mini Mental State Examination, the Disability Assessment for Dementia, and the Visual Paired Associates Test of delayed recall from the Wechsler Memory Scale, as compared to patients without such antibodies (Hock, C. et al., 2003, *Neuron*, 38:547-554).

It has been shown previously, that the benzothiazole amyloid-imaging PET tracer {N-methyl-$^{11}$C}2-[4'-(methylamino)phenyl]6-hydroxybenzothiazole ([$^{11}$C]PIB) shows a clear difference in retention between AD patients and control subjects, and that [$^{11}$C]PIB retention follows the known topography of amyloid deposition in AD brain (Klunk, et al., 2004, Ann. Neurol., 55(3):306-19). To determine whether benzothiazole amyloid imaging probes might be sensitive to changes in brain amyloid deposition caused by an anti-amyloid therapy in general, testing by immunization with AN-1792 was performed. Studies were performed for the binding of {N-methyl-3H}2-[4'-(methylamino)phenyl]6-hydroxy-benzothiazole ([$^{3}$H]PIB) to homogenates of frontal cortex and cerebellum obtained from control subjects (n=4), AD patients (n=5) and from a single AN-1792-treated AD case (in duplicate). See, e.g., Example 9. The frontal cortex of AD patients showed elevated [$^{3}$H]PIB binding compared to control brain. However, [$^{3}$H]PIB binding to the AN-1792-treated brain showed no increase in [$^{3}$H]PIB binding over control frontal cortex. Taken together, these data suggest that benzothiazole amyloid imaging probes which are useful as PET tracers, such as [$^{11}$C]PIB, could detect changes in amyloid deposition in AD brain induced by AN-1792 treatment and by other therapies that have a significant effect on brain amyloid deposition in AD.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

The following examples are given to illustrate the present invention. It should be understood, however, that the invention is not to be limited to the specific conditions or details described in these examples. Throughout the specification, any and all references to a publicly available document, including U.S. patents, are specifically incorporated into this patent application by reference.

EXAMPLES

Compounds of formulas (I) and (II), and the formulae of structures 1-45, can be prepared by methods that are well known in the art. See, e.g., WO 02/16333 and U.S. Patent Publication No. 2003/0236391, published Dec. 25, 2003, the entire contents of which are herein incorporated by reference.

All of the reagents used in the synthesis were purchased from Aldrich Chemical Company and used without further purification, unless otherwise indicated. Melting points were determined on MeI-TEMP II and were uncorrected. The $^1$H NMR spectra of all compounds were measured on Bruker 300 using TMS as internal reference and were in agreement with the assigned structures. The TLC was performed using Silica Gel 60 $F_{254}$ from EM Sciences and detected under UV lamp. Flash chromatography was performed on silica gel 60 (230-400 mesh. Purchased from Mallinckrodt Company. The reverse phase TLC were purchased from Whiteman Company.

General Methodology for Synthesis of Compound of Formula (I):

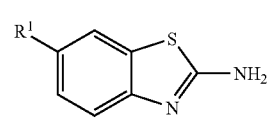

I $R^1$ is hydrogen, —OH, —NO$_2$, —CN, —COOR, —OCH$_2$OR, $C_1$-$C_6$ alkyl, $C_2$-$C_6$ alkenyl, $C_2$-$C_6$ alkynyl, $C_1$-$C_6$ alkoxy or halo, wherein one or more of the atoms of $R^1$ may be a radiolabeled atom;

R is $C_1$-$C_6$ alkyl, wherein one or more of the carbon atoms may be a radiolabeled atom;

is hydrolysed by one of the following two procedures:

Preparation of 2-aminothiophenol via hydrolysis

The 6-substituted 2-aminobenzothiazole (172 mmol) is suspended in 50% KOH (180 g KOH dissolved in 180 mL water) and ethylene glycol (40 mL). The suspension is heated to reflux for 48 hours. Upon cooling to room temperature, toluene (300 mL) is added and the reaction mixture is neutralized with acetic acid (180 mL). The organic layer is separated and the aqueous layer is extracted with another 200 mL of toluene. The toluene layers are combined and washed with water and dried over MgSO$_4$. Evaporation of the solvent gives the desired product.

Preparation of 2-aminothiophenol via hydrazinolysis

The 6-substituted -benzothiazole (6.7 mmol) is suspended in ethanol (11 mL, anhydrous) and hydrazine (2.4 mL) is added under a nitrogen atmosphere at room temperature. The reaction mixture is heated to reflux for 1 hour. The solvent is evaporated and the residue is dissolved into water (10 mL) and adjusted to a pH of 5 with acetic acid. The precipitate is collected with filtration and washed with water to give the desired product.

The resulting 5-substituted-2-amino-1-thiophenol of the form

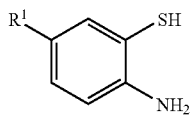

is coupled to a benzoic acid of the form:

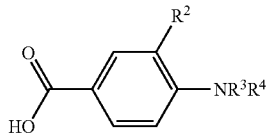

wherein $R^2$ is hydrogen, and $R^3$ and $R^4$ are independently hydrogen, $C_1$-$C_6$ alkyl, $C_2$-$C_6$ alkenyl or $C_2$-$C_6$ alkynyl by the following methodology:

A mixture of the 5-substituted 2-aminothiophenol (4.0 mmol), the benzoic acid (4.0 mmol), and polyphosphoric acid (PPA) (10 g) is heated to 220° C. for 4 hours. The reaction mixture is cooled to room temperature and poured into 10% potassium carbonate solution (~400 mL). The precipitate is collected by filtration under reduced pressure to give the desired product, which can be purified by flash chromatography or recrystallization.

The $R^2$ hydrogen can be substituted with either a non-radioactive halo or a radioactive halo by the following reaction:

To a solution of 6-substituted 2-(4'-aminophenyl)-benzothiazole (1 mg) in 250 µL acetic acid in a sealed vial is added 40 µL of chloramine-T solution (28 mg dissolved in 500 µL acetic acid) followed by 27 µL (ca. 5 mCi) of sodium [$^{125}$I]iodide (specific activity 2,175 Ci/mmol). The reaction mixture is stirred at room temperature for 2.5 hours and quenched with saturated sodium hydrogensulfite solution. After dilution with 20 ml of water, the reaction mixture is loaded onto C8 Plus SepPak and eluted with 2 ml methanol. Depending on the nature of the substituent on the 6-position, protecting groups may need to be employed. For example, the 6-hydroxy group is protected as the methanesulfonyl (mesyloxy) derivative. For deprotection of the methanesulfonyl group, 0.5 ml of 1 M NaOH is added to the eluted solution of radioiodinated intermediate. The mixture is heated at 50° C. for 2 hours. After being quenched by 500 µL of 1 M acetic acid, the reaction mixture is diluted with 40 mL of water and loaded onto a C8 Plus SepPak. The radioiodinated product, having a radioactivity of ca. 3 mCi, is eluted off the SepPak with 2 mL of methanol. The solution is condensed by a nitrogen stream to 300 µL and the crude product is purified by HPLC on a Phenomenex ODS column (MeCN/TEA buffer, 35:65, pH 7.5, flow rate 0.5 mL/minute up to 4 minutes, 1.0 mL/minute at 4-6 minutes, and 2.0 mL/minute after 6 minutes, retention time 23.6). The collected fractions are loaded onto a C8 Plus SepPak. Elution with 1 mL of ethanol gave ca. 1 mCi of the final radioiodinated product.

When either or both $R^3$ and $R^4$ are hydrogen, then $R^3$ and $R^4$ can be converted to $C_1$-$C_6$ alkyl, $C_2$-$C_6$ alkenyl or $C_2$-$C_6$ alkynyl by reaction with an alkyl, alkenyl or alkynyl halide under the following conditions:

For dialkylation: To a solution of 6-substituted 2-(4'-aminophenyl)-benzothiazole (0.59 mmol) in DMSO (anhydrous, 2 ml) are added alkyl, alkenyl, or alkynyl halide (2.09 mmol), and $K_2CO_3$ (500 mg, 3.75 mmol). The reaction mixture is heated at 140° C. for 16 hours. Upon cooling to room temperature, the reaction mixture is poured into water and extracted with ethyl acetate (3×10 mL). The organic layers are combined and the solvent is evaporated. The residue is purified by flash column to give the desired 6-substituted dimethylaminophenyl)-benzothiazole.

For monoalkylation: To a solution of 6-substituted 2-(4'-aminophenyl)-benzothiazole (0.013 mmol) in DMSO (anhydrous, 0.5 ml) is added alkyl, alkenyl, or alkynyl halide (0.027 mmol) and anhydrous $K_2CO_3$ (100 mg, 0.75 mmol). The reaction mixture is heated at 100° C. for 16 hours. Upon cooling to room temperature, the reaction mixture is directly purified by normal phase preparative TLC to give the desired 6-substituted-2-(4'-methylaminophenyl)-benzothiazole derivatives.

When $R^2$ is hydrogen or a non-radioactive halo, $R^4$ is $C_1$-$C_6$ alkyl, $C_2$-$C_6$ alkenyl or $C_2$-$C_6$ alkynyl, wherein the alkyl, alkenyl or alkynyl comprises a radioactive carbon or is substituted with a radioactive halo, the compound can be synthesized by one of the following sequences:

For Radioactive Carbon Incorporation:

Approximately 1 Ci of [$^{11}$C]carbon dioxide is produced using a CTI/Siemens RDS 112 negative ion cyclotron by irradiation of a nitrogen gas ($^{14}N_2$) target containing 1% oxygen gas with a 40 µA beam current of 11 MeV protons for 60 minutes. [$^{11}$C]Carbon dioxide is converted to [$^{11}$C]methyl iodide by first reacting it with a saturated solution of lithium aluminum hydride in THF followed by the addition of hydriodic acid at reflux temperature to generate [$^{11}$C]methyl iodide. The [$^{11}$C]methyl iodide is carried in a stream of nitrogen gas to a reaction vial containing the precursor for radiolabeling. The precursor, 6-substituted 2-(4'-aminophenyl)-benzothiazole (~3.7 µmoles), is dissolved in 400 µL of DMSO. Dry KOH (10 mg) is added, and the 3 mL V-vial is vortexed for 5 minutes. No-carrier-added [$^{11}$C]methyl iodide is bubbled through the solution at 30 mL/minute at room temperature. The reaction is heated for 5 minutes at 95° C. using an oil bath. The reaction product is purified by semi-preparative HPLC using a Prodigy ODS-Prep column eluted with 60% acetonitrile/40% triethylammonium phosphate buffer pH 7.2 (flow at 5 mL/minute for 0-7 minutes then increased to 15 mL/minute for 7-30 minutes). The fraction containing [N-methyl-$^{11}$C] 6-substituted 2-(4'-methylaminophenyl)-benzothiazole (at about 15 min) is collected and diluted with 50 mL of water and eluted through a Waters C18 SepPak Plus cartridge. The C18 SepPak is washed with 10 mL of water, and the product is eluted with 1 mL of ethanol (absolute) into a sterile vial followed by 14 mL of saline. Radiochemical and chemical purities are >95% as determined by analytical HPLC (k'=4.4 using the Prodigy ODS(3) analytical column eluted with 65/35 acetonitrile/triethylammonium phosphate buffer pH 7.2). The radiochemical yield averages 17% at EOS based on [$^{11}$C]methyl iodide, and the specific activity averages about 160 GBq/µmol (4.3 Ci/µmol) at end of synthesis.

For Radioactive Halogen Incorporation:

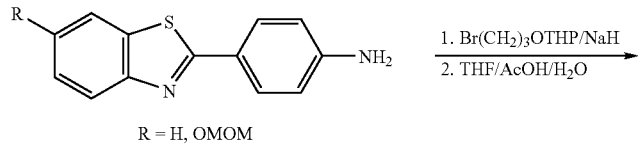

R = H, OMOM

-continued

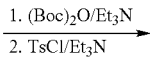
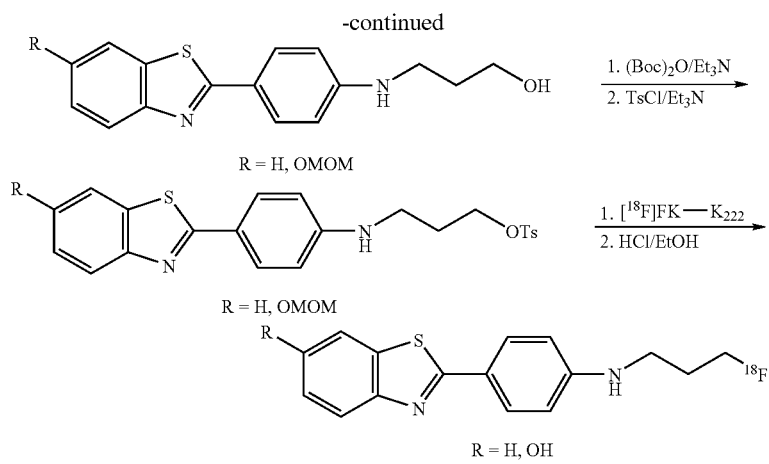

A mixture of 6-substituted 2-(4'-aminophenyl)-benzathiazole (protecting groups may be necessary depending on the nature of the 6-substituent as noted above) (0.22 mmol), NaH (4.2 mmol) and 2-(-3-bromopropoxy)tetrahydro-2-H-pyran (0.22 mmol) in THF (8 mL) is heated to reflux for 23 hours. The solvent is removed by distillation and the residue is dissolved in to ethyl acetate and water, the organic layer is separated and the aqueous layer is extracted with ethyl acetate (10 mL×6). The organic layer is combined and dried over $MgSO_4$ and evaporated to dryness. The residue is added $AcOH/THF/H_2O$ solution (5 mL, 4/2/1) and heated to 100° C. for 4 hours. The solvent is removed by evaporation and the residue is dissolved in ethyl acetate (~10 mL) washed by $NaHCO_3$ solution, dried over $MgSO_4$ and evaporated to dryness to give a residue which is purified with preparative TLC(hexane:ethyl acetate=60:40) to give the desired 6-substituted 2-(4'-(3"-hydroxypropylamino)-phenyl)-benzathiazole (45%).

To a solution of 6-substituted 2-(4'-(3"-hydroxypropylamino) -phenyl)-benzathiazole (0.052 mmol) and $Et_3N$ (0.5 ml) dissolved in acetone (5 mL) is added $(Boc)_2O$ (50 mg, 0.22 mmol). The reaction mixture is stirred at room temperature for 6 hours followed by addition of tosyl chloride (20 mg, 0.11 mmol). The reaction mixture is stirred at room temperature for another 24 hours. The solvent is removed and the residue is dissolved into ethyl acetate (10 mL), washed with $NaCO_3$ solution, dried over $MgSO_4$, evaporated, and purified with flash column (Hexane/ethyl acetate=4/1) to give the desired 6-substituted 2-(4'-(3"-toluenesulfonoxypropylamino)-phenyl)-benzothiazole (13%). This 6-substituted 2-(4'-(3"-toluenesulfonoxypropylamino)-phenyl)-benzothiazole is then radiofluorinated by standard methods as follows:

A cyclotron target containing 0.35 mL of 95% [0-18]-enriched water is irradiated with 11 MeV protons at 20 µA of beam current for 60 minutes, and the contents are transferred to a 5 mL reaction vial containing Kryptofix 222 (22.3 mg) and $K_2CO_3$ (7.9 mg) in acetonitrile (57 µL). The solution is evaporated to dryness three times at 110° C. under a stream of argon following the addition of 1 mL aliquots of acetonitrile. To the dried [F-18]fluoride is added 3 mg of 6-substituted 2-(4'-(3"-toluenesulfonoxypropylamino)-phenyl)-benzothiazole in 1 mL DMSO, and the reaction vial is sealed and heated to 85° C. for 30 minutes. To the reaction vial, 0.5 mL of MeOH/HCl (concentrated) (2/1 v/v) is added, and the vial is heated at 120° C. for 10 minutes. After heating, 0.3 mL of 2 M sodium acetate buffer is added to the reaction solution followed by purification by semi-prep HPLC using a Phenomenex Prodigy ODS-prep C18 column (10 µm250×10 mm) eluted with 40% acetonitrile/60% 60 mM triethylamine-phosphate buffer (v/v) pH 7.2 at a flow rate of 5 mL/minute for 15 minutes, then the flow is increased to 8 mL/minute for the remainder of the separation. The product, [F-18]6-substituted 2-(4'-(3"-fluoropropylamino)-phenyl)-benzothiazole, is eluted at 20 minutes in a volume of about 16 mL. The fraction containing [F-18]6-substituted 2-(4'-(3"-fluoropropylamino) -phenyl)-benzothiazole is diluted with 50 mL of water and eluted through a Waters C18 SepPak Plus cartridge. The SepPak cartridge is then washed with 10 mL of water, and the product is eluted using 1 mL of ethanol (absol.) into a sterile vial. The solution is diluted with 10 mL of sterile normal saline for intravenous injection into animals. The [F-18]6-substituted 2-(4'-(3"-fluoropropylamino)-phenyl)-benzothiazole product is obtained in 2-12% radiochemical yield at the end of the 120 minute radiosynthesis (not decay corrected) with an average specific activity of 1500 Ci/mmol.

Example 1

[N-Methyl-$^{11}$C]2-(4'-Dimethylaminophenyl)-6-methoxy -benzothiazole was synthesized according to Scheme I

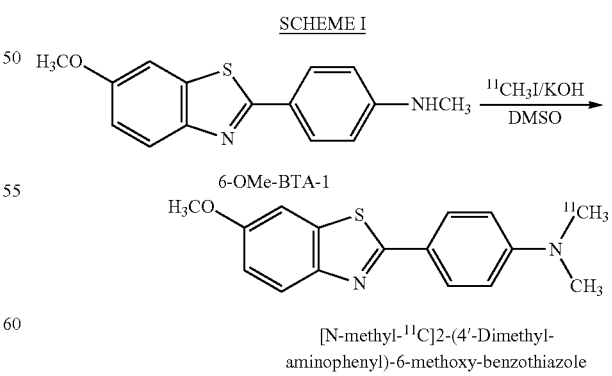

[N-methyl-$^{11}$C]2-(4'-Dimethyl-aminophenyl)-6-methoxy-benzothiazole

Approximately 1 Ci of [$^{11}$C]carbon dioxide was produced using a CTI/Siemens RDS 112 negative ion cyclotron by irradiation of a nitrogen gas ($^{14}N_2$) target containing 1% oxygen gas with a 40 µA beam current of 11 MeV protons for 60 minutes. [$^{11}$C]Carbon dioxide is converted to [$^{11}$C]methyl iodide by first reacting it with a saturated solution of lithium aluminum hydride in THF followed by the addition of hydriodic acid at reflux temperature to generate [$^{11}$C]methyl iodide. The [$^{11}$C]methyl iodide is carried in stream of nitrogen gas to a reaction vial containing the precursor for radiolabeling. The precursor, 6-CH$_3$O-BTA-1 (1.0 mg, 3.7 μmoles), was dissolved in 400 μL of DMSO. Dry KOH (10 mg) was added, and the 3 mL V-vial was vortexed for 5 minutes. No-carrier-added [$^{11}$C]methyl iodide was bubbled through the solution at 30 mL/minute at room temperature. The reaction was heated for 5 minutes at 95° C. using an oil bath. The reaction product was purified by semi-preparative HPLC using a Prodigy ODS-Prep column eluted with 60% acetonitrile/40% triethylammonium phosphate buffer pH 7.2 (flow at 5 mL/minute for 0-7 minutes then increased to 15 mL/minute for 7-30 minutes). The fraction containing [N-Methyl-$^{11}$C]2-(4'-Dimethylaminophenyl)-6-methoxy-benzothiazole (at about 15 minutes) was collected and diluted with 50 mL of water and eluted through a Waters C18 SepPak Plus cartridge. The C18 SepPak was washed with 10 mL of water, and the product was eluted with 1 mL of ethanol (absolute) into a sterile vial followed by 14 mL of saline. Radiochemical and chemical purities were >95% as determined by analytical HPLC (k'=4.4 using the Prodigy ODS(3) analytical column eluted with 65/35 acetonitrile/triethylammonium phosphate buffer pH 7.2). The radiochemical yield averaged 17% at EOS based on [$^{11}$C]methyl iodide, and the specific activity averaged about 160 GBq/μmol (4.3 Ci/μmol) at end of synthesis.

Example 2

2-(3'-$^{125}$I-iodo-4'-amino-phenyl)-benzothiazol-6-ol was synthesized according to Scheme II

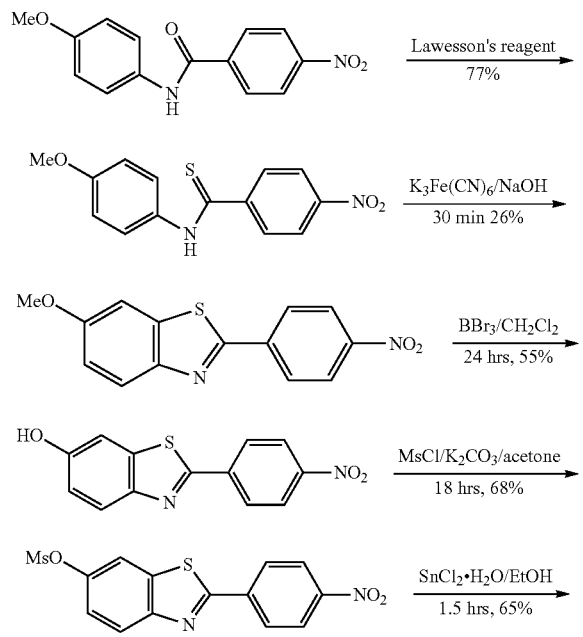

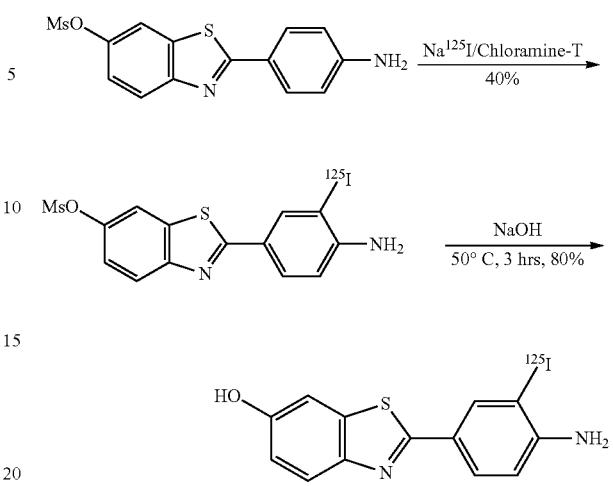

To a solution of 2-(4'-aminophenyl)-6-methanesulfonoxy-benzothiazole (1 mg) in 250 μL acetic acid in a sealed vial was added 40 μL of chloramine T solution (28 mg dissolved in 500 μL acetic acid) followed by 27 μL (ca. 5 mCi) of sodium [$^{125}$I]iodide (specific activity 2,175 Ci/mmol). The reaction mixture was stirred at room temperature for 2.5 hours and quenched with saturated sodium hydrogensulfite solution. After dilution with 20 ml of water, the reaction mixture was loaded onto C8 Plus SepPak and eluted with 2 ml methanol. For deprotection of the methanesulfonyl group, 0.5 ml of 1 M NaOH was added to the eluted solution of radioiodinated intermediate. The mixture was heated at 50° C. for 2 hours. After being quenched by 500 μL of 1 M acetic acid, the reaction mixture was diluted with 40 mL of water and loaded onto a C8 Plus SepPak. The radioiodinated product, having a radioactivity of ca. 3 mCi, was eluted off the SepPak with 2 mL of methanol. The solution was condensed by a nitrogen stream to 300 μL and the crude product was purified by HPLC on a Phenomenex ODS column (MeCN/TEA buffer, 35:65, pH 7.5, flow rate 0.5 mL/minute up to 4 minutes, 1.0 mL/minute at 4-6 minutes, and 2.0 mL/minute after 6 minutes, retention time 23.6). The collected fractions were loaded onto a C8 Plus SepPak. Elution with 1 mL of ethanol gave ca. 1 mCi of the final radioiodinated product.

Preparation of the $^{123}$I radiolabeled derivatives, proceeds similarly to the synthesis outlined above. For example, replacing sodium [$^{125}$I]iodide with sodium [$^{123}$I]iodide in the synthetic method would provide the $^{123}$I radiolabeled compound. Such substitution of one radiohalo atom for another is well known in the art, see for example, Mathis C A, Taylor S E, Biegon A, Enas J D. [$^{125}$I]5-Iodo-6-nitroquipazine: a potent and selective ligand for the 5-hydroxytryptamine uptake complex I. In vitro studies. *Brain Research* 1993; 619:229-235; Jagust W, Eberling J L, Roberts J A, Brennan K M, Hanrahan S M, Van Brocklin H, Biegon A, Mathis C A. In vivo imaging of the 5-hydroxytryptamine reuptake site in primate brain using SPECT and [$^{123}$I]5-iodo-6-nitroquipazine. *European Journal of Pharmacolgy* 1993; 242:189-193; Jagust W J, Eberling J L, Biegon A, Taylor S E, Van-Brocklin H, Jordan S, Hanrahan S M, Roberts J A, Brennan K M, Mathis C A. [Iodine-123]5-Iodo-6-Nitroquipazine: SPECT Radiotracer to Image the Serotonin Transporter. *Journal of Nuclear Medicine* 1996; 37:1207-1214.)

Example 3

2-(3-$^{18}$F-Fluoro-4-methylamino-phenyl)-benzothiazol-6-ol was synthesized according to Scheme III Scheme III

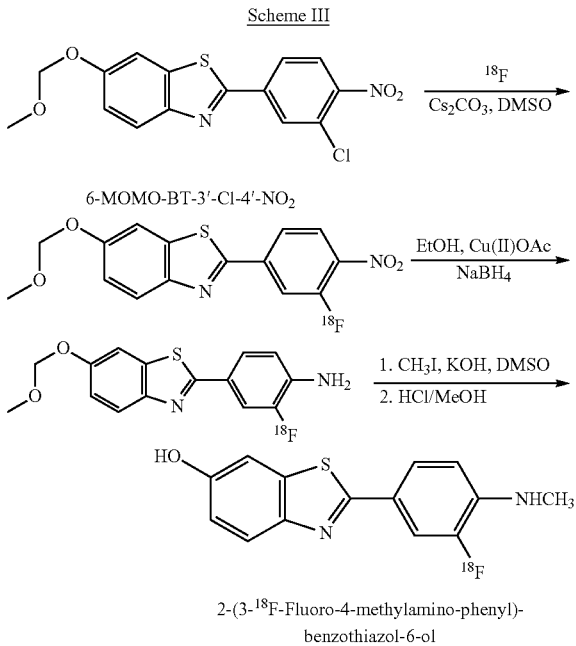

2-(3-$^{18}$F-Fluoro-4-methylamino-phenyl)-benzothiazol-6-ol

A cyclotron target containing 0.35 mL of 95% [0-18]-enriched water was irradiated with 11 MeV protons at 20 μA of beam current for 60 minutes, and the contents were transferred to a 5 mL reaction vial containing 2 mg $Cs_2CO_3$ in acetonitrile (57 μL). The solution was evaporated to dryness at 110° C. under a stream of argon three times using 1 mL aliquots of acetonitrile. To the dried [F-18]fluoride was added 6 mg of 6-MOMO-BT-3'-Cl-4'-$NO_2$ in 1 mL DMSO, and the reaction vial was sealed and heated to 120° C. for 20 minutes (radiochemical incorporation for this first radiosynthesis step was about 20% of solubilized [F-18]fluoride). To the crude reaction mixture was added 8 mL of water and 6 mL of diethyl ether, the mixture was shaken and allowed to separate. The ether phase was removed and evaporated to dryness under a stream of argon at 120° C. To the dried sample, 0.5 mL of absolute EtOH was added along with 3 mg copper (II) acetate and 8 mg of $NaBH_4$. The reduction reaction was allowed to proceed for 10 minutes at room temperature (the crude yield for the reduction step was about 40%). To the reaction mixture was added 8 mL of water and 6 mL of diethyl ether, the mixture was shaken and the ether phase separated. The diethyl ether phase was dried under a stream of argon at 120° C. To the reaction vial, 700 uL of DMSO was added containing 30 micromoles of $CH_3I$ and 20 mg of dry KOH. The reaction vial was heated at 120° C. for 10 minutes. A solution of 700 uL of 2:1 MeOH/HCl (concentrated) was added and heated for 15 minutes at 120° C. After heating, 1 mL of 2 M sodium acetate buffer was added to the reaction solution followed by purification by semi-prep HPLC using a Phenomenex Prodigy ODS-prep C18 column (10 μm 250×10 mm) eluted with 35% acetonitrile/65% 60 mM triethylamine-phosphate buffer (v/v) pH 7.2 at a flow rate of 5 mL/minute for 2 minutes, then the flow was increased to 15 mL/minute for the remainder of the separation. The product, 2-(3-$^{18}$F-fluoro-4-methylamino-phenyl) benzothiazol-6-ol, eluted at ~15 minutes in a volume of about 16 mL. The fraction containing 2-(3-$^{18}$F-fluoro-4-methylamino-phenyl)-benzothiazol-6-ol was diluted with 50 mL of water and eluted through a Waters C18 SepPak Plus cartridge. The SepPak cartridge was then washed with 10 mL of water, and the product was eluted using 1 mL of ethanol (absol.) into a sterile vial. The solution was diluted with 10 mL of sterile normal saline for intravenous injection into animals. The 2-(3-$^{18}$F-fluoro-4-methylamino-phenyl)-benzothiazol-6-ol product was obtained in 0.5% (n=4) radiochemical yield at the end of the 120 minute radiosynthesis (not decay corrected) with an average specific activity of 1000 Ci/mmol. The radiochemical and chemical purities of 2-(3-$^{18}$F-fluoro-4-methylamino-phenyl)-benzothiazol-6-ol were assessed by radio-HPLC with UV detection at 350 nm using a Phenomenex Prodigy ODS (3) C18 column (5 μm, 250×4.6 mm) eluted with 40% acetonitrile/60% 60 mM triethylamine-phosphate buffer (v/v) pH 7.2. 2-(3-$^{18}$F-Fluoro-4-methylamino-phenyl)-benzothiazol-6-ol had a retention time of ~11 minutes at a flow rate of 2 mL/min (k'=5.5). The radiochemical purity was >99%, and the chemical purity was >90%. The radiochemical identity of 2-(3-$^{18}$F-Fluoro-4-methylamino-phenyl)-benzothiazol-6-ol was confirmed by reverse phase radio-HPLC utilizing a quality control sample of the final radiochemical product co-injected with a authentic (cold) standard.

Example 4

2-[4-(3-$^{18}$F-Fluoro-propylamino)-phenyl]-benzothiazol-6-ol was synthesized according to Scheme IV Scheme IV

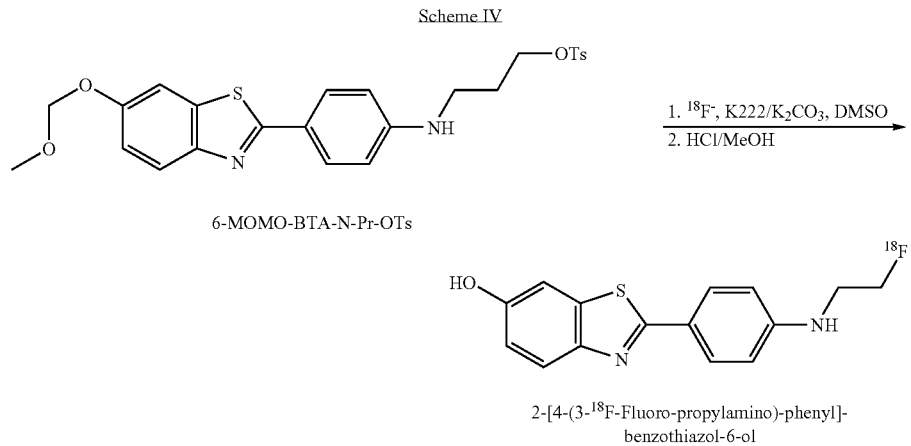

2-[4-(3-$^{18}$F-Fluoro-propylamino)-phenyl]-benzothiazol-6-ol

A cyclotron target containing 0.35 mL of 95% [0-18]-enriched water was irradiated with 11 MeV protons at 20 μA of beam current for 60 minutes, and the contents were transferred to a 5 mL reaction vial containing Kryptofix 222 (22.3 mg) and $K_2CO_3$ (7.9 mg) in acetonitrile (57 μL). The solution was evaporated to dryness three times at 110° C. under a stream of argon following the addition of 1 mL aliquots of acetonitrile. To the dried [F-18]fluoride was added 3 mg of 6-MOMO-BTA -N-Pr-Ots in 1 mL DMSO, and the reaction vial was sealed and heated to 85° C. for 30 minutes. To the reaction vial, 0.5 mL of MeOH/HCl (concentrated) (2/1 v/v) was added, and the vial was heated at 120° C. for 10 minutes. After heating, 0.3 mL of 2 M sodium acetate buffer was added to the reaction solution followed by purification by semi-prep HPLC using a Phenomenex Prodigy ODS-prep C18 column (10 μm 250×10 mm) eluted with 40% acetonitrile/60% 60 mM triethylamine-phosphate buffer (v/v) pH 7.2 at a flow rate of 5 mL/minute for 15 minutes, then the flow was increased to 8 mL/minute for the remainder of the separation. The product, [F-18]6-HO-BTA-N-PrF, eluted at ~20 minutes in a volume of about 16 mL. The fraction containing [F-18]6-HO-BTA-N-PrF was diluted with 50 mL of water and eluted through a Waters C18 SepPak Plus cartridge. The SepPak cartridge was then washed with 10 mL of water, and the product was eluted using 1 mL of ethanol (absol.) into a sterile vial. The solution was diluted with 10 mL of sterile normal saline for intravenous injection into animals. The [F-18]6-HO-BTA-N-PrF product was obtained in 8±4% (n=8) radiochemical yield at the end of the 120 minute radiosynthesis (not decay corrected) with an average specific activity of 1500 Ci/mmol. The radiochemical and chemical purities of [F-18]6-HO-BTA-N-PrF were assessed by radio-HPLC with UV detection at 350 nm using a Phenomenex Prodigy ODS(3) C18 column (5 μm, 250×4.6 mm) eluted with 40% acetonitrile/60% 60 mM triethylamine-phosphate buffer (v/v) pH 7.2. [F-18]6-HO-BTA-N-PrF had a retention time of 12 minutes at a flow rate of 2 mL/minute (k'=6.1). The radiochemical purity was >99%, and the chemical purity was >90%. The radiochemical identity of [F-18]6-HO-BTA-N-PrF was confirmed by reverse phase radio-HPLC utilizing a quality control sample of the final radiochemical product co-injected with a authentic (cold) standard.

Example 5

Synthesis of 2-(3'-iodo-4'-aminophenyl)-6-hydroxy benzothiazole

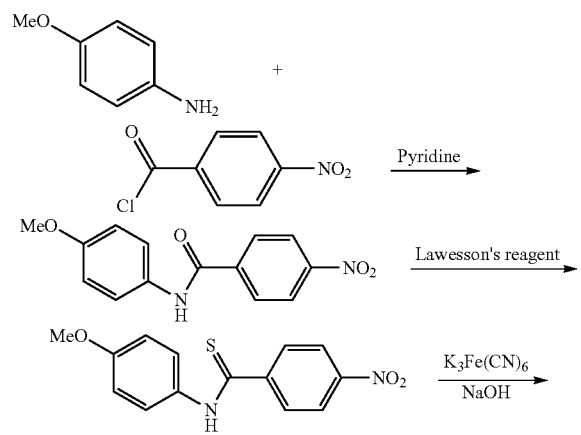

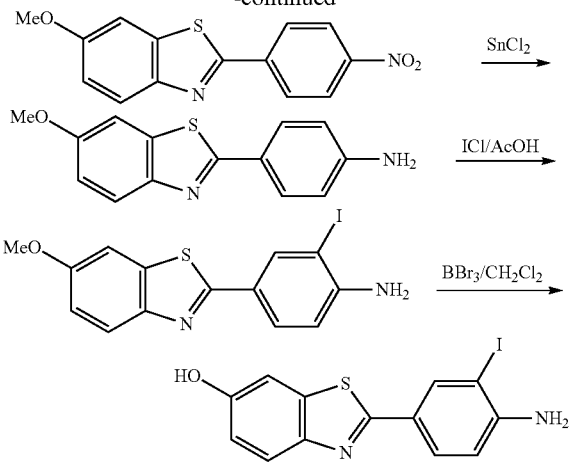

Preparation of 4-Methoxy-4'-nitrobenzanilide p-Anisidine (1.0 g, 8.1 mmol) was dissolved in anhydrous pyridine (15 ml), 4-nitrobenzoyl chloride (1.5 g, 8.1 mmol) was added. The reaction mixture was allowed to stand at room temperature for 16 hrs. The reaction mixture was poured into water and the precipitate was collected with filtrate under vacuum pressure and washed with 5% sodium bicarbonate (2×10 ml). The product was used in the next step without further purification. $^1$HNMR (300 MHz, DMSO-$d_6$) δ: 10.46 (s, 1H, NH), 8.37 (d, J=5.5 Hz, 2H, H-3',5'), 8.17 (d, J=6.3 Hz, 2H, H-2',6'), 7.48 (d, J=6.6 Hz, 2H), 6.97 (d, J=6.5 Hz, 2H), 3.75 (s, 3H, MeO).

Preparation of 4-Methoxy-4'-nitrothiobenzanilide

A mixture of 4-methoxy-4'-nitrothiobenzaniline (1.0 g, 3.7 mmol) and Lawesson's reagent (0.89 g, 2.2 mmol, 0.6 equiv.) in chlorobenzene (15 mL) was heated to reflux for 4 hrs. The solvent was evaporated and the residue was purified with flush column (hexane:ethyl acetate=4:1) to give 820 mg (77.4%) of the product as orange color solid. $^1$HNMR (300 MHz, DMSO-$d_6$) δ: 8.29 (d, 2H, H-3',5'), 8.00 (d, J=8.5 Hz, 2H, H-2',6'), 7.76 (d, 2H), 7.03 (d, J=8.4 Hz, 2H), 3.808.37 (d, J=5.5 Hz, 2H, H-3',5'), 8.17 (d, J=6.3 Hz, 2H, H-2',6'), 7.48 (d, J=6.6 Hz, 2H), 6.97 (d, J=6.5 Hz, 2H), 3.75 (s, 3H, MeO). (s, 3H, MeO).

Preparation of 6-Methoxy-2-(4-nitrophenyl)benzothiazole

4-Methoxy-4'-nitrothiobenzanilides (0.5 g, 1.74 mmol) was wetted with a little ethanol (~0.5 mL), and 30% aqueous sodium hydroxide solution (556 mg 13.9 mmol. 8 equiv.) was added. The mixture was diluted with water to provide a final solution/suspension of 10% aqueous sodium hydroxide. Aliquots of this mixture were added at 1 min intervals to a stirred solution of potassium ferricyanide (2.29 g, 6.9 mmol, 4 equiv.) in water (5 mL) at 80-90° C. The reaction mixture was heated for a further 0.5 h and then allowed to cool. The participate was collected by filtration under vacuum pressure and washed with water, purified with flush column (hexane: ethyl acetate=4:1) to give 130 mg (26%) of the product. $^1$HNMR (300 MHz, Acetone-$d_6$) δ: 8.45 (m, 4H), 8.07 (d, J=8.5 Hz, 1H, H-4), 7.69 (s, 1H, H-7), 7.22 (d, J=9.0 Hz, 1H, H-5), 3.90 (s, 3H, MeO)

Preparation of 6-Methoxy-2-(4-aminophenyl)benzothiazole

A mixture of the 6-methoxy-2-(4-nitrophenyl)benzothiazoles (22 mg, 0.077 mmol) and tin(II) chloride (132 mg, 0.45 mmol) in boiling ethanol was stirred under nitrogen for 4 hrs. Ethanol was evaporated and the residue was dissolved in ethyl acetate (10 mL), washed with 1 N sodium hydroxide (2 mL) and water (5 mL), and dried over $MgSO_4$. Evaporation of the solvent gave 19 mg (97%) of the product as yellow solid.

Preparation of 2-(3'-Iodo-4'-aminophenyl)-6-methoxybenzothiazole

To a solution of 2-(4'-aminophenyl)-6-methoxy benzothiazole (22 mg, 0.09 mmol) in glacial acetic acid (2.0 mL) was injected 1 M iodochloride solution in $CH_2Cl_2$ (0.10 mL, 0.10 mmol, 1.2 eq.) under $N_2$ atmosphere. The reaction mixture was stirred at room temperature for 16 hr. The glacial acetic acid was removed under reduced pressure and the residue was dissolved in $CH_2Cl_2$. After neutralizing the solution with $NaHCO_3$, the aqueous layer was separated and extracted with $CH_2Cl_2$. The organic layers were combined and dried over $MgSO_4$. Following the evaporation of the solvent, the residue was purified by preparative TLC(Hexanes:ethyl acetate=6:1) to give 2-(4'-amino-3'-iodophenyl)-6-methoxy benzothiazole (25 mg, 76%) as brown solid. $^1$HNMR (300 MHz, $CDCl_3$) δ (ppm): 8.35 (d, J=2.0 Hz, 1H), 7.87 (dd, $J_1$=2.0 Hz, $J_2$=9.0 Hz, 1H), 7.31 (d, J=2.2 Hz, 1H), 7.04 (dd, $J_1$=2.2 Hz, $J_2$=9.0 Hz, 1H), 6.76 (d, J=9.0 Hz, 1H), 3.87 (s, 3H).

Preparation of 2-(3'-Iodo-4'-aminophenyl)-6-hydroxybenzothiazole

To a solution of 2-(4'-Amino-3'-iodophenyl)-6-methoxy benzothiazole (5) (8.0 mg, 0.02 mmol) in $CH_2Cl_2$ (2.0 mL) was injected 1 M $BBr_3$ solution in $CH_2Cl_2$ (0.20 ml, 0.20 mmol) under $N_2$ atmosphere. The reaction mixture was stirred at room temperature for 18 hrs. After the reaction was quenched with water, the mixture was neutralized with $NaHCO_3$. The aqueous layer was extracted with ethyl acetate (3×3 mL). The organic layers were combined and dried over $MgSO_4$. The solvent was then evaporated under reduced pressure and the residue was purified by preparative TLC (Hexanes:ethyl acetate=7:3) to give 2-(3'-iodo-4'-aminophenyl)-6-hydroxybenzothiazole (4.5 mg, 58%) as a brown solid. $^1$HNMR (300 MHz, acetone-$d_6$) δ (ppm): 8.69 (s, 1H), 8.34 (d, J=2.0 Hz, 1H), 7.77 (dd, $J_1$=2.0 Hz, $J_2$=8.4 Hz, 1H), 7.76 (d, J=8.8 Hz, 1H), 7.40 (d, J=2.4 Hz, 1H), 7.02 (dd, $J_1$=2.5 Hz, $J_2$=8.8 Hz, 1H), 6.94 (d, J=8.5 Hz, 1H), 5.47 (br., 2H). HRMS m/z 367.9483 (M+calcd for $C_{13}H_9N_2OSI$ 367.9480).

Example 6

Synthesis of 2-(3'-iodo-4'-methylaminophenyl)-6-hydroxybenzothiazole

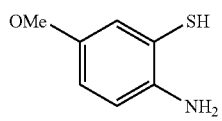

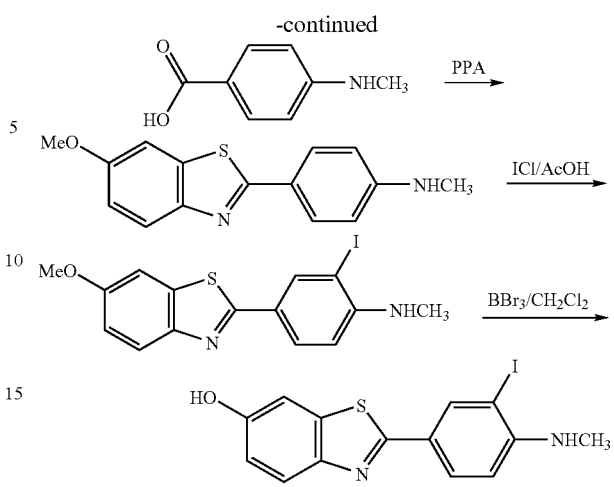

Preparation of 6-Methoxy-2-(4-methylaminophenyl)benzothiazole

A mixture of 4-methylaminobenzoic acid (11.5 g, 76.2 mmol) and 5-methoxy-2-aminothiophenol (12.5, g, 80 mmol) was heated in PPA (~30 g) to 170° C. under $N_2$ atmosphere for 1.5 hr. The reaction mixture was then cooled to room temperature and poured into 10% $K_2CO_3$ solution. The precipitate was filtered under reduced pressure. The crude product was re-crystallized twice from acetone/water and THF/water followed by the treatment with active with carbon to give 4.6 g (21%) of 6-Methoxy-2-(4-methylaminophenyl)benzothiazole as a yellow solid. $^1$HNMR (300 MHz, acetone-$d_6$) δ: 7.84 (d, J=8.7 Hz, 2H, H-2' 6'), 7.78 (dd, $J_1$=8.8 Hz, $J_2$=1.3 Hz, 1H, H-4), 7.52 (d, J=2.4 Hz, 1H, H-7), 7.05 (dd, $J_1$=8.8 Hz, $J_2$=2.4 Hz, H-5), 6.70 (d, J=7.6 Hz, 2H, H-3' 5'), 5.62 (s, 1H, NH), 3.88 (s, 3H, $OCH_3$), 2.85 (d, J=6.2 Hz, 3H, $NCH_3$)

Preparation of 2-(3'-Iodo-4'-methylaminophenyl)-6-methoxy benzothiazole

To a solution of 2-(4'-Methylaminophenyl)-6-methoxy benzothiazole (20 mg, 0.074 mmol) dissolved in glacial acetic acid (2 mL) was added Icl (90 μL, 0.15 mmol, 1.2 eq, 1M in $CH_2Cl_2$) under $N_2$. The reaction was allowed to stir at room temperature for 18 hr. The glacial acetic acid was then removed under reduced pressure. The residue was dissolved in $CH_2Cl_2$ and neutralized with $NaHCO_3$. The aqueous layer was extracted with $CH_2Cl_2$ and the organic layers were combined, dried over $MgSO_4$ and evaporated. The residue was purified with preparative TLC (Hexane:EA=2:1) to give 2-(4'-methylamino-3'-iodophenyl)-6-methoxy benzothiazole (8 mg, 27%) as brown solid. $^1$HNMR (300 MHz, $CDCl_3$)δ (ppm):8.39 (d, J=2.0 Hz, 1H), 7.88 (d, J=9.0 Hz, 1H), 7.33 (d, J=2.2 Hz, 1H), 7.06 (dd, $J_1$=2.2 Hz, $J_2$=9.0 Hz, 1H), 6.58 (d, J=9.0 Hz, 1H), 3.89 (s, 3H, $OCH_3$).

Preparation of 2-(3'-Iodo-4'-methylamino-phenyl)-6-hydroxy benzothiazole

To a solution of 2-(4'-methylamino-3'-iodophenyl)-6-methoxy benzothiazole (12 mg, 0.03 mmol) dissolved in $CH_2Cl_2$ (4 mL) was added $BBr_3$ (400 μl, 0.4 mmol, 1M in $CH_2Cl_2$) under $N_2$. The reaction was allowed to stir at room temperature for 18 hr. Water was then added to quench the reaction and the solution was neutralized with NaHCO$_3$, extracted with ethyl acetate (3×5 mL). The organic layers were combined, dried over MgSO$_4$ and evaporated. The residue was purified with preparative TLC (Hexane:EA=7:3) to give 2-(4'-methylamino-3'-iodophenyl)-6-hydroxy benzothiazole (5 mg, 43%) as brown solid. $^1$HNMR (300 MHz, CDCl$_3$) δ(ppm): 8.37 (d, H=2.0 Hz, 1H), 7.88 (dd, J$_1$=2.0 Hz, J$_2$=8.4 Hz, 1H), 7.83 (d, J=8.8 Hz, 1H), 7.28 (d, J=2.4 Hz, 1H), 6.96 (dd, J$_1$=2.5 Hz, J$_2$=8.8 Hz, 1H), 6.58 (d, J=8.5 Hz, 1H), 2.96 (s, 3H, CH$_3$).

Example 7

Radiosynthesis of [$^{125}$I]6-OH-BTA-0-3'-I

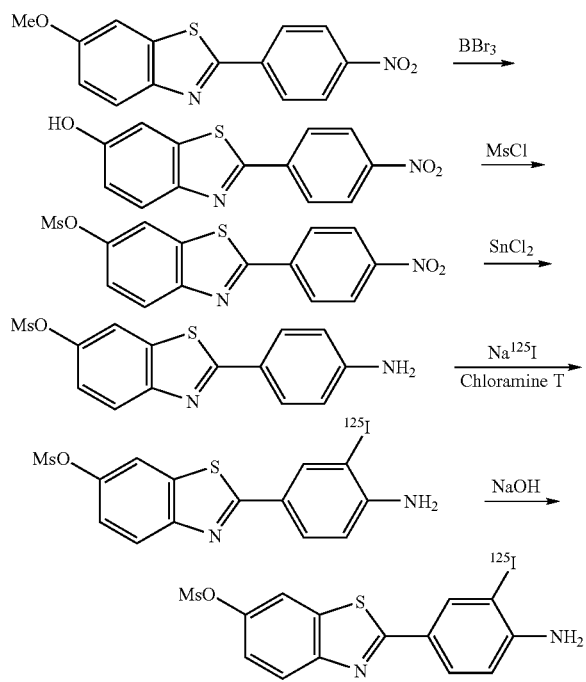

Preparation of 2-(4'-Nitrophenyl)-6-hydroxybenzothiazole

To a suspension of 2-(4'-nitrophenyl)-6-methoxy benzothiazole (400 mg, 1.5 mmol) in CH$_2$Cl$_2$ (10 mL) was added BBr$_3$ (1M in CH$_2$Cl$_2$, 10 mL, 10 mmol). The reaction mixture was stirred at room temperature for 24 hr. The reaction was then quenched with water, and extracted with ethyl acetate (3×20 mL). The organic layers were combined and washed with water, dried over MgSO$_4$, and evaporated. The residue was purified by flash chromatography (silica gel, hexanes: ethyl acetate=1:1) to give the product as a yellow solid (210 mg, 55%). $^1$HNMR (300 MHz, Acetone-d$_6$) δ (Ppm): 9.02 (s, OH), 8.41 (d, J=9.1 Hz, 1H), 8.33 (d, J=9.1 Hz, 1H), 7.96 (d, J=8.6 Hz, 1H), 7.53 (d, J=2.4 Hz, 1H), 7.15 (dd, J1=8.6 Hz, J2=2.4 Hz, 1H).

Preparation of 2-(4'-Nitrophenyl)-6-methylsulfoxy benzothiazole

To a solution of 2-(4'-nitrophenyl)-6-hydroxy benzothiazole (50 mg, 0.18 mmol) dissolved in acetone (7 mL, anhydrous) was added K$_2$CO$_3$ (100 mg, 0.72 mmol, powdered) and MsCl (200 ul). After stirring for 2 hrs, the reaction mixture was filtered. The filtrate was concentrated and the residue was purified by flash column (silica gel, hexane:ethyl acetate=4:1) to give 2-(4-nitrophenyl)-6-methylsulfoxy benzothiazole (44 mg, 68%) as pale yellow solid. $^1$HNMR (30 MHz, acetone-d$_6$) δ (ppm): 8.50-8.40 (m, 4H), 8.29 (d, J=2.3 Hz, 1H), 8.23 (d, J=8.9 Hz, 1H), 7.61 (dd, J$_1$=2.3 Hz, J$_2$=8.9 Hz, 1H).

Preparation of 2-(4'-Aminophenyl)-6-methylsulfoxy benzothiazole

To a solution of 2-(4'-nitrophenyl)-6-methylsulfoxy benzothiazole (35 mg, 0.10 mmol) dissolved in ethanol (10 mL) was added SnCl$_2$.2H$_2$O (50 mg). The reaction mixture was heated to reflux for 1.5 hr. The solvent was then removed under reduced pressure. The residue was dissolved in ethyl acetate (10 mL), washed with 1N NaOH, water, dried over MgSO$_4$. Evaporation of the solvent afforded 2-(4'-aminophenyl)-6-methylsulfoxy benzothiazole (21 mg, 65%) as pale brown solid. $^1$HNMR (300 MHz, CDCl$_3$) δ (ppm): 8.02 (d, J=6.2 Hz, 1H), 7.92 (d, J=8.7 Hz, 2H), 7.84 (d, J=2.4 Hz, 1H), 7.38 (dd, J$_1$=2.4 Hz, J$_2$=6.2 Hz, 1H), 6.78 (d, J=8.7 Hz, 2H), 2.21 (s, 3H, CH$_3$).

Example 8

Radiosynthesis of [$^{125}$I]6-OH-BTA-1-3'-I

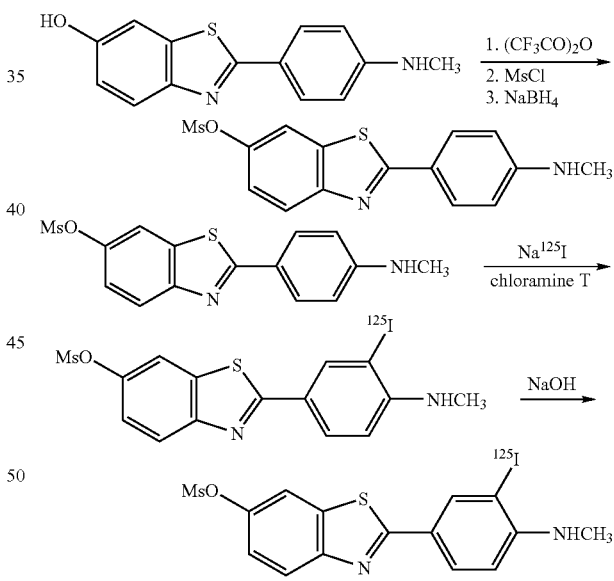

To a solution of 2-(4'-methylaminophenyl)-6-hydroxy benzothiazole (300 mg, 1.17 mmol) dissolved in CH$_2$Cl$_2$ (20 mL) was added Et$_3$N (2 mL) and trifluoroacetic acid (1.5 mL). The reaction mixture was stirred at room temperature for 3 h. The solvent was removed under reduced pressure and the residue was dissolved in ethyl acetate (30 mL), washed with NaHCO$_3$ solution. Brine, water, and dried over MgSO$_4$. After evaporation of the solvent, the residue was dissolved in acetone (20 ml, pre-dried over K$_2$CO$_3$), K$_2$CO$_3$ (1.0 g, powered) was added followed by MsCl (400 mg, 3.49 mmol). The reaction mixture was stirred at room temperature and monitored with TLC omog starting material disappeared. The residue was then filtrated. The filtrate was evaporated under reduced pressure. The residue was dissolved in ethyl acetate (30 mL), washed with NaHCO$_3$ solution. Brine, water, and dried over MgSO$_4$. After evaporation of the solvent, the residue was dissolved in EtOH and NaBH$_4$ was added. The reaction mixture was stirred at room temperature for 2 h. The solvent was evaporated and the residue was dissolved in water, extracted with ethyl acetate (20 ml×3), the extracts were combined and dried over MgSO$_4$. After evaporation of the solvent, the residue was purified with flash column (hexanes/ethyl acetate=8:1) to give the product (184 mg, 47.0%) as brown solid. $^1$HNMR (300 MHz, CDCl$_3$) δ (ppm): 7.94 (d, J=8.8 Hz, 1H), 7.87 (d, J=8.7 Hz, 2H), 7.77 (d, J=2.3 Hz, 1H), 7.30 (dd, J$_1$=8.8 Hz, J$_2$=2.3 Hz, 1H), 6.63 (d, J=8.7 Hz, 2H), 3.16 (s, CH$_3$), 2.89 (s, NCH$_3$).

General Procedures for Radiolabelling:

To a solution of 2-(4'-aminophenyl)-6-methanesulfonoxy benzothiazole or 2-(4'-methylaminophenyl)-6-methylsulfoxy benzothiazole (1 mg) in 250 μL acetic acid in a sealed vial was added 40 μL of chloramines T solution (28 mg dissolved in 500 μL acetic acid) followed by 27 μL (ca. 5 mCi) of sodium [$^{125}$I]iodide (specific activity 2,175 Ci/mmol). The reaction mixture was stirred at r.t. for 2.5 hrs and quenched with saturated sodium hydrogensulfite solution. After dilution with 20 ml of water, the reaction mixture was loaded onto C8 Plus SepPak and eluted with 2 ml methanol. For deprotection of the methanesulfonyl group, 0.5 ml of 1 M NaOH was added to the eluted solution of radioiodinated intermediate. The mixture was heated at 50° C. for 2 hours. After being quenched by 500 μL of 1 M acetic acid, the reaction mixture was diluted with 40 mL of water and loaded onto a C8 Plus SepPak. The radioiodinated product, having a radioactivity of ca. 3 mCi, was eluted off the SepPak with 2 mL of methanol. The solution was condensed by a nitrogen stream to 300 μL and the crude product was purified by HPLC on a Phenomenex ODS column (MeCN/TEA buffer, 35:65, pH 7.5, flow rate 0.5 mL/min up to 4 min, 1.0 mL/min at 4-6 min, and 2.0 mL/min after 6 min, retention time 23.6). The collected fractions were loaded onto a C8 Plus SepPak. Elution with 1 mL of ethanol gave ca. 1 mCi of the final radioiodinated product.

Example 9

Treatment with AN-1792 Vaccine Decreases the Binding of the Amyloid Tracer, PIB, to Brain Homogenates The benzothiazole amyloid-imaging PET tracer {N-methyl-$^{11}$C}2-[4'-(methylamino)phenyl]6-hydroxybenzothiazole ("[$^{11}$C]PIB") shows a clear difference in retention between AD patients and control subjects. This [$^{11}$C]PIB retention follows the known topography of amyloid deposition in AD brain (Klunk et al. 2004, *Ann. Neurol.*, 55(3):306-19). To determine whether the present benzothiazole amyloid imaging probes are sensitive to changes in brain amyloid deposition caused by an anti-amyloid therapy in general, studies were performed for the binding of {N-methyl-3H}2-[4'-(methylamino)phenyl]6-hydroxy-benzothiazole ([$^{13}$H] PIB) to homogenates of postmortem brain from two AN-1792-treated AD cases. Frozen blocks of frontal, temporal and parietal cortex and cerebellum from control brains (n=4), AD brains (n=5) and from two brains from the AN-1792 trial were obtained (Ferrer et al. 2004, *Brain Pathology* 14, 11-20; Masliah et al. 2005, *Neurology* 64, 129-131). The blocks were sectioned (40 mm) and every second section was submitted for histological analysis with antibodies specific for Aβ40 or Aβ42 or the fluorescent derivative of Congo red, X-34 (beta-sheet specific). Intervening sections were combined and homogenized in Tris-buffered saline with protease inhibitors. An aliquot was submitted for Aβ ELISA and another aliquot was assayed for [$^3$H]PIB binding after dilution with phosphate-buffered saline (100 mg tissue, incubated with 1 nM [$^3$H]PIB, filtered, washed and counted to determine bound [$^3$H]PIB).

Figure 2:
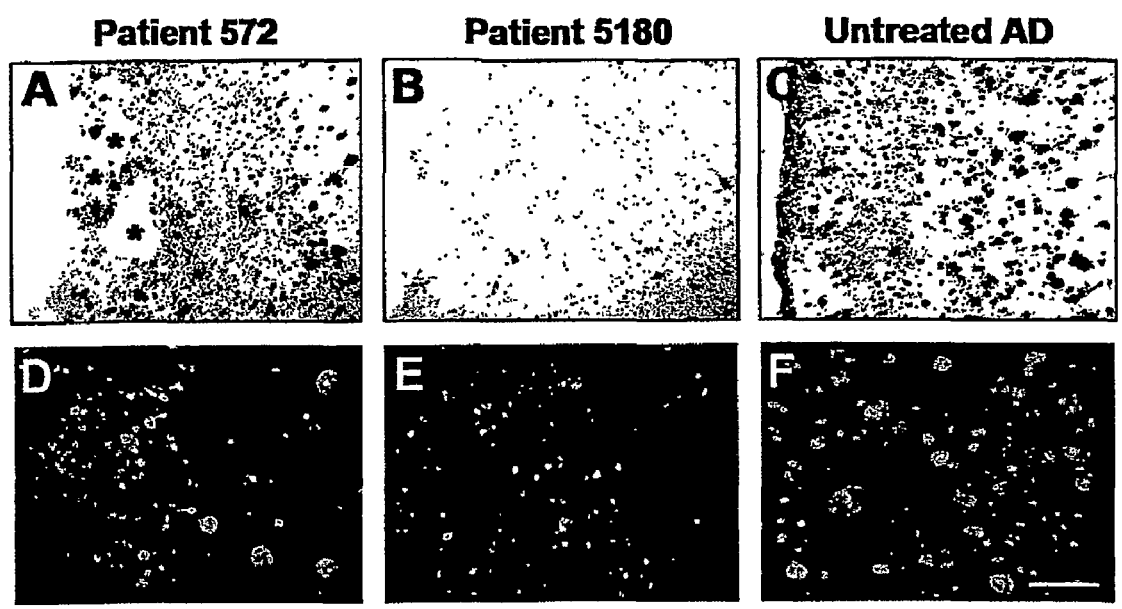
FIG. 2 shows Aβ42 immunoreactivity (ir) and X-34 histofluorescent labeling of β-pleated sheet in the temporal cortex of AD patients 572 (A,D) and 5180 (B,E), compared to a representative end-stage AD patient (C,F). Scale bar=200 μm. Large areas devoid of plaques in case 572 are marked with asterisks. Case 5180 is devoid of plaques, but shows some neurofibrollary tangles and neuritic elements stained by X-34.
Figure 3:
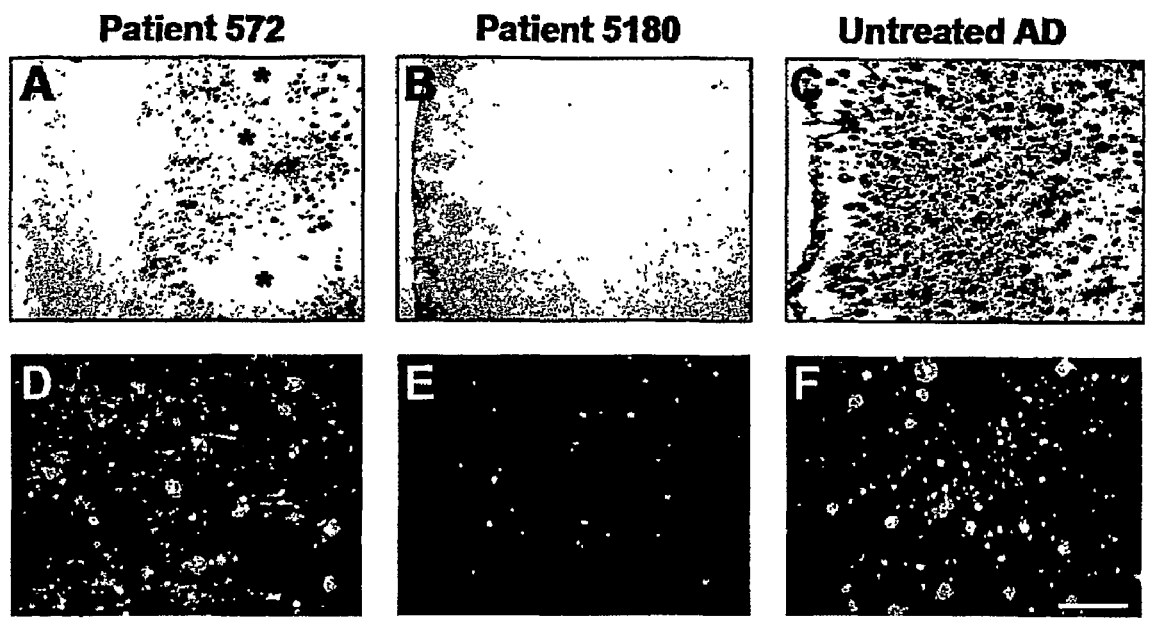
FIG. 3 shows Aβ42 immunoreactivity and X-34 histofluorescent labeling of β-pleated sheet in the frontal cortex of patients 572 (A,D) and 5180 (B,E), compared to a representative end-stage Alzheimer's disease patient. Scale bar=200 μm. Areas devoid of plaques in case 572 are marked with asterisks. Case 5180 is devoid of plaques, but shows some neurofibrollary tangles stained by X-34 (see FIG. 4).
Figure 4:
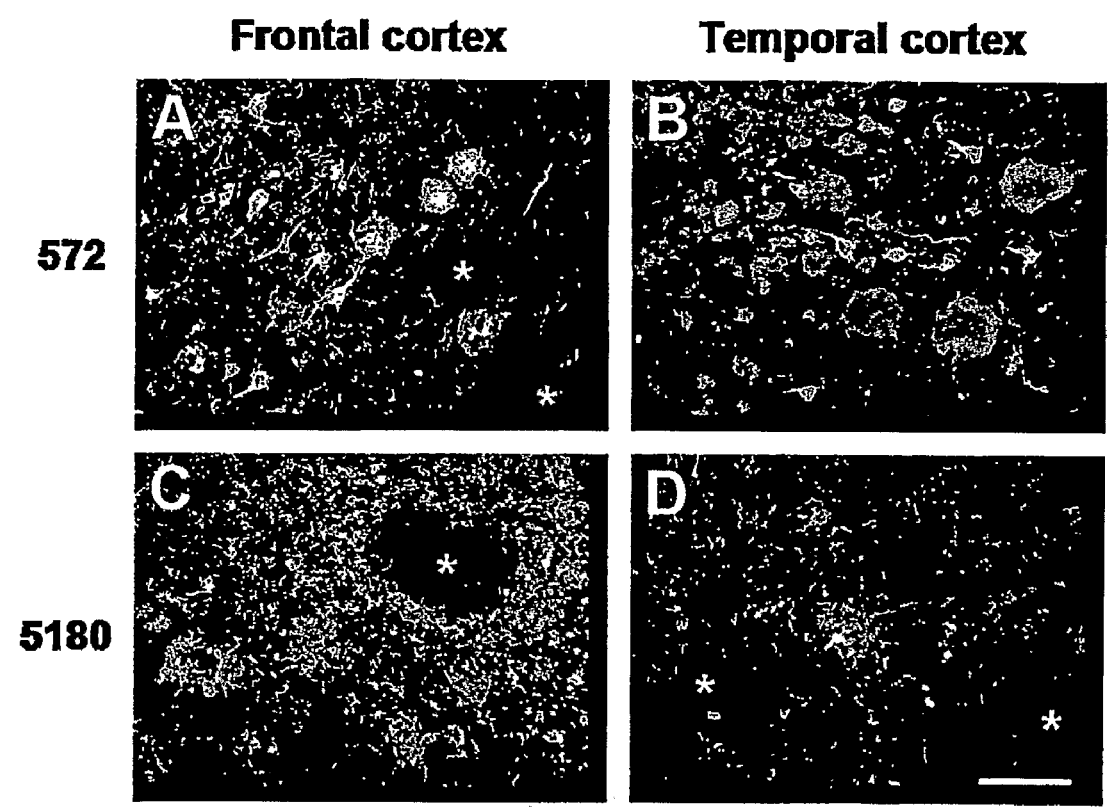
FIG. 4 shows X-34 staining of β-pleated sheet-containing neurofibrillary tangles, neuropil threads, dystrophic neurites and senile plaques in patients 572 and 5180. Note that patient 5180 has abundant neuritic elements, but no plaques. Areas cleared of X-34 stained elements are marked with asterisks. These cleared areas strongly suggest the presence of plaques before AN-1792 treatment. Scale bar=100 μm.
Figure 5:
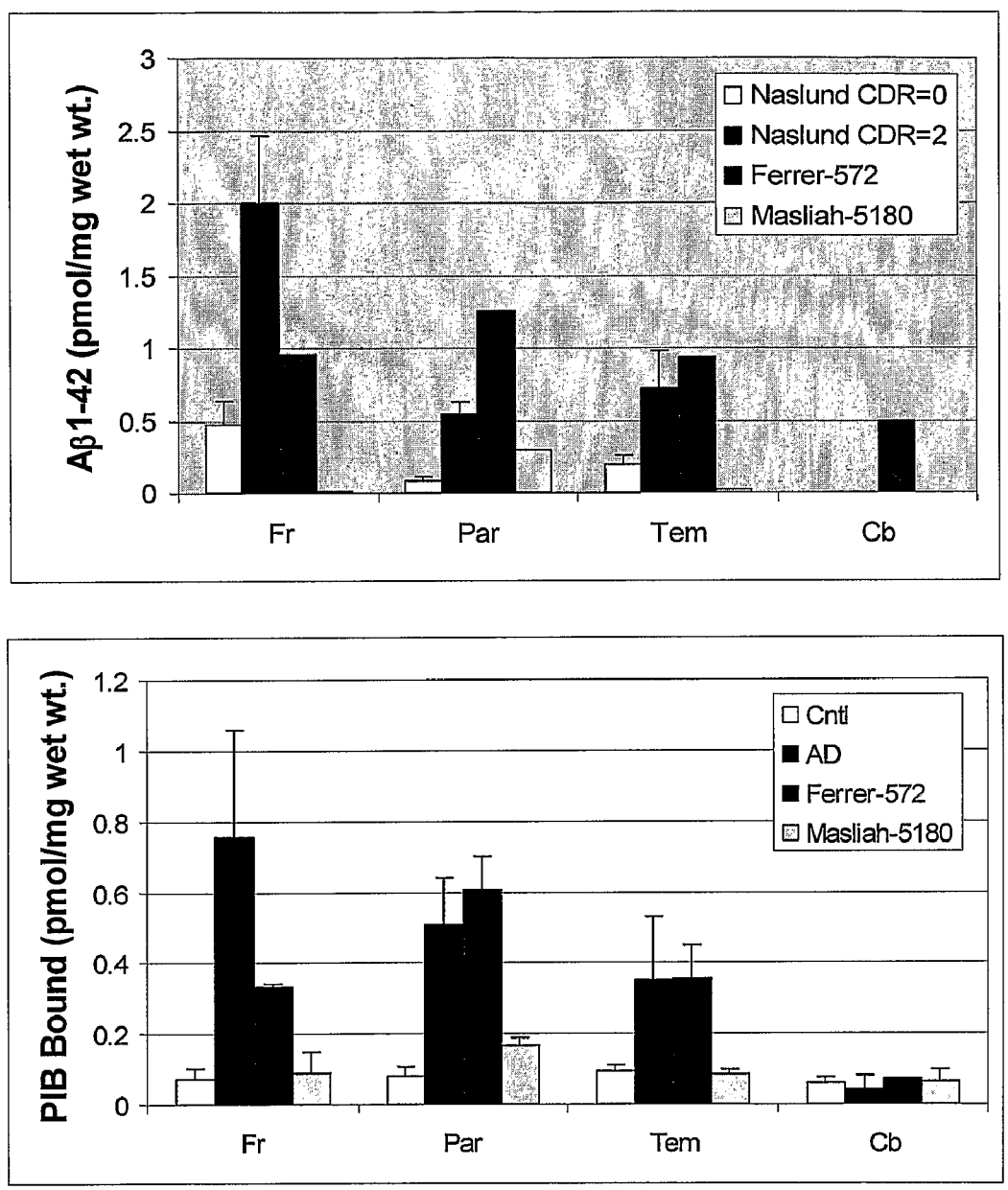
FIG. 5: The top graph charts ELISA data for Aβ42 in cases 572 and 5180 in frontal, parietal, temporal and cerebellar cortices. These are compared to published data for the frontal, parietal and temporal cortices of elderly controls and AD subjects (Naslund et al. 2000, *Jama* 283, 1571-1577). The bottom graph charts [$^3$H]PIB binding in cases 572 and 5180 in frontal, parietal, temporal and cerebellar cortices, compared to [$^3$H]PIB binding to the same areas of elderly controls (n=4) and AD subjects (n=5). Note that [$^3$H]PIB binding correlates well with ELISA and histologic data in FIGS. 2-4.

Neuropathologically, these brains were remarkable for a focal absence of plaques in several cortical areas (FIGS. 2-4). The Masliah case (case# 5180) was remarkably devoid of plaques (FIGS. 2-4) and showed basal levels of Aβ and [$^3$H] PIB binding (FIG. 5). The Ferrer case (case #572) showed most apparent decreases in plaque deposition in the frontal cortex (FIGS. 3 and 4), which correlated with lower levels of Aβ and [$^3$H]PIB binding (FIG. 5).

These findings support the following conclusions:
1. PIB Binding provides evidence of decreased amyloid load in AN-1792-treated cases.
2. The decreases in PIB binding correlate with histological evidence for plaque removal and with ELISA evidence for Aβ removal.
3. It should be possible to detect in vivo decreases in amyloid load that are caused by anti-amyloid therapies.

In addition, the focal nature of amyloid clearance means the entire brain would be monitored, and PET imaging is well-suited for this Other embodiments of the invention will be apparent to those skilled in the art from consideration of the specification and practice of the invention disclosed herein. It is intended that the specification be considered as exemplary only, with the true scope and spirit of the invention being indicated by the following claims.

As used herein and in the following claims, singular articles such as "a", "an", and "one" are intended to refer to singular or plural.

What Is claimed is:

1. A method of determining the efficacy of therapy in the treatment of amyloidosis, comprising:
   (A) administering to a patient in need thereof an effective amount of a compound selected from the group consisting of structures 1, 3-5, 8-16, 18, and 20-45, wherein at least one substituent moiety in the compound comprises a detectable label selected from the group consisting of $^3$H, $^{131}$I, $^{125}$I, $^{123}$I, $^{76}$Br, $^{75}$Br, $^{18}$F, $^{19}$F, $^{77}$C, $^{13}$C, and $^{14}$C:

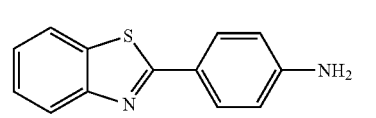

1

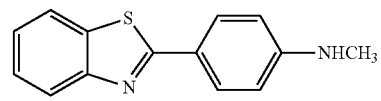

3

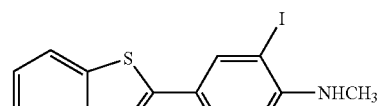

4

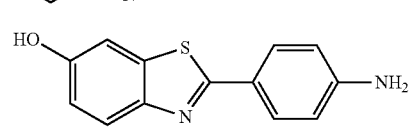

5

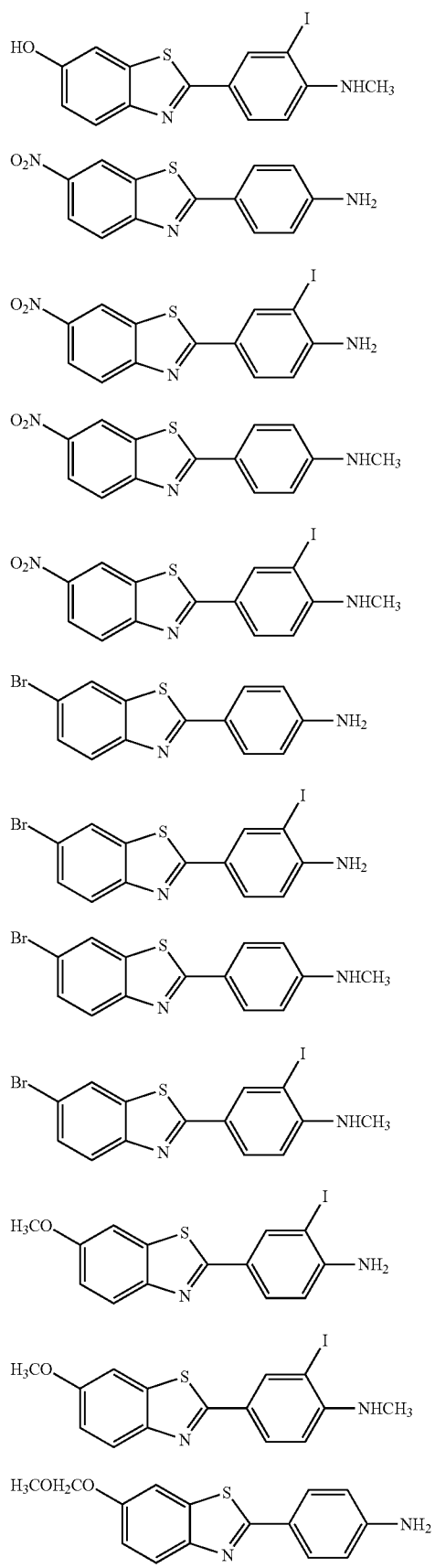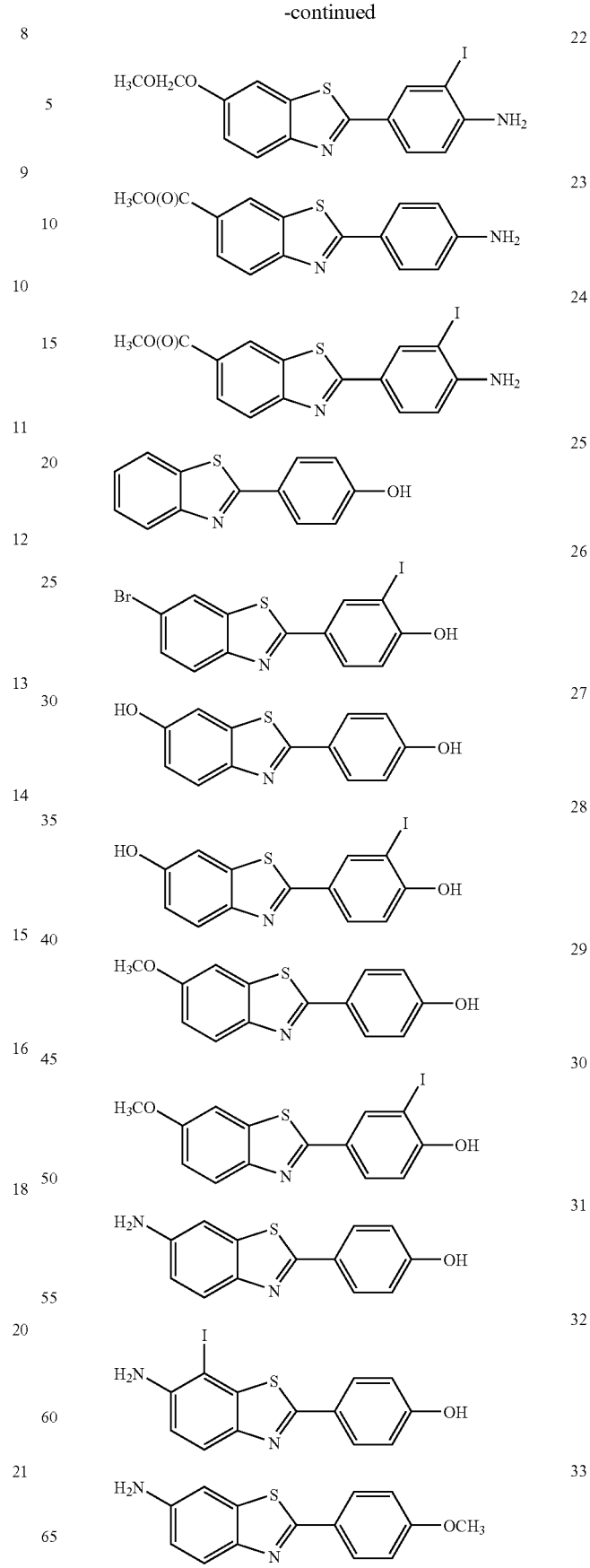

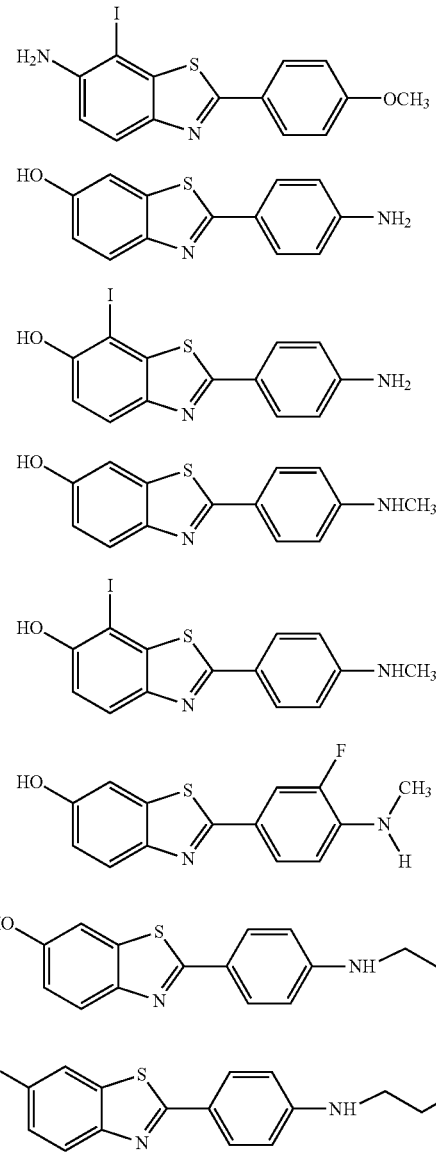

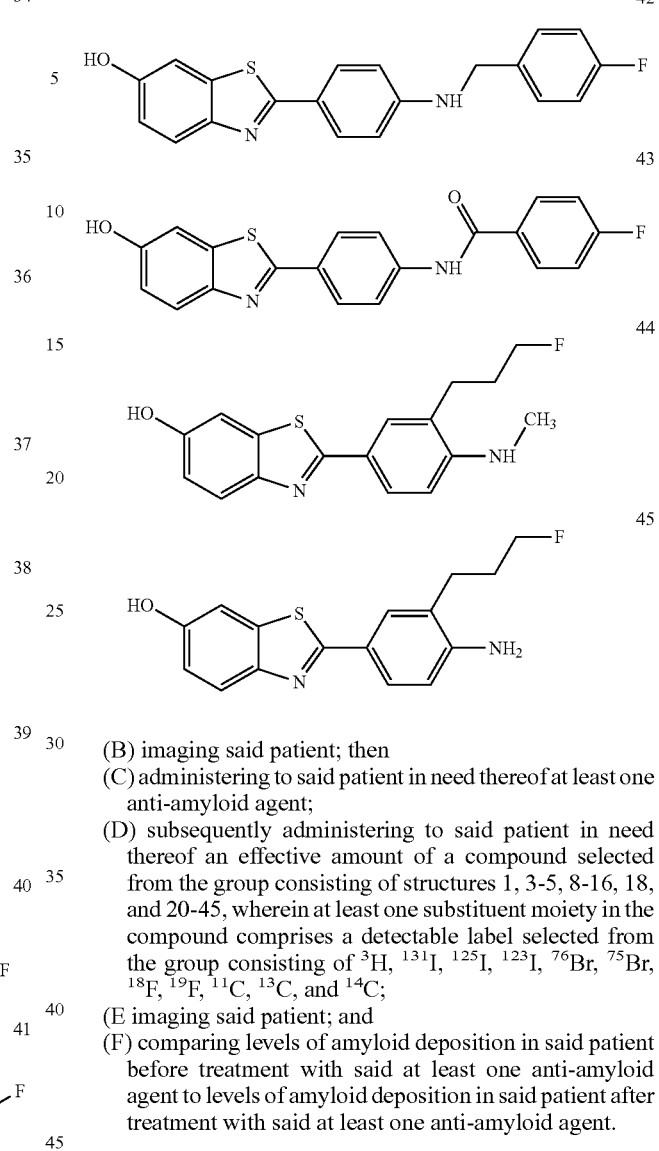

(B) imaging said patient; then
(C) administering to said patient in need thereof at least one anti-amyloid agent;
(D) subsequently administering to said patient in need thereof an effective amount of a compound selected from the group consisting of structures 1, 3-5, 8-16, 18, and 20-45, wherein at least one substituent moiety in the compound comprises a detectable label selected from the group consisting of $^{3}H$, $^{131}I$, $^{125}I$, $^{123}I$, $^{76}Br$, $^{75}Br$, $^{18}F$, $^{19}F$, $^{11}C$, $^{13}C$, and $^{14}C$;
(E imaging said patient; and
(F) comparing levels of amyloid deposition in said patient before treatment with said at least one anti-amyloid agent to levels of amyloid deposition in said patient after treatment with said at least one anti-amyloid agent.

* * * * *